(12) United States Patent
Hauser et al.

(10) Patent No.: US 9,067,084 B2
(45) Date of Patent: Jun. 30, 2015

(54) AMPHIPHILIC LINEAR PEPTIDE/PEPTOID AND HYDROGEL COMPRISING THE SAME

(75) Inventors: Charlotte A. E. Hauser, Singapore (SG); Ulung Gondo Kusumo Khoe, Singapore (SG); Archana Mishra, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 13/638,152

(22) PCT Filed: Dec. 15, 2010

(86) PCT No.: PCT/SG2010/000469
§ 371 (c)(1),
(2), (4) Date: Sep. 28, 2012

(87) PCT Pub. No.: WO2011/123061
PCT Pub. Date: Oct. 6, 2011

(65) Prior Publication Data
US 2013/0023460 A1 Jan. 24, 2013

Related U.S. Application Data

(60) Provisional application No. 61/319,838, filed on Mar. 31, 2010.

(51) Int. Cl.
| | | |
|---|---|---|
| A61K 38/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |
| C12N 5/00 | (2006.01) | |
| C12N 5/02 | (2006.01) | |
| A61Q 19/00 | (2006.01) | |
| A61K 8/04 | (2006.01) | |
| A61K 8/64 | (2006.01) | |
| C07K 5/062 | (2006.01) | |
| C07K 5/072 | (2006.01) | |
| C07K 5/083 | (2006.01) | |
| C07K 5/103 | (2006.01) | |
| C07K 7/06 | (2006.01) | |

(52) U.S. Cl.
CPC .............. *A61Q 19/00* (2013.01); *A61K 8/042* (2013.01); *A61K 8/64* (2013.01); *A61K 38/00* (2013.01); *C07K 5/06026* (2013.01); *C07K 5/06043* (2013.01); *C07K 5/06052* (2013.01); *C07K 5/0606* (2013.01); *C07K 5/06069* (2013.01); *C07K 5/06104* (2013.01); *C07K 5/06113* (2013.01); *C07K 5/0806* (2013.01); *C07K 5/0808* (2013.01); *C07K 5/1008* (2013.01); *C07K 5/101* (2013.01); *C07K 7/06* (2013.01)

(58) Field of Classification Search
CPC ...................................................... A61K 38/02
See application file for complete search history.

(56) References Cited

U.S. PATENT DOCUMENTS

| | | | | | |
|---|---|---|---|---|---|
| 5,258,287 | A | * | 11/1993 | Baxter et al. | 435/69.1 |
| 5,723,129 | A | * | 3/1998 | Potter et al. | 424/200.1 |
| 6,204,359 | B1 | * | 3/2001 | Delaey et al. | 530/322 |
| 7,413,877 | B2 | * | 8/2008 | Collier et al. | 435/71.1 |
| 2002/0068346 | A1 | * | 6/2002 | Krystek et al. | 435/190 |
| 2006/0084607 | A1 | * | 4/2006 | Spirio et al. | 514/13 |

FOREIGN PATENT DOCUMENTS

| | | | |
|---|---|---|---|
| WO | WO 2009039854 A2 | * | 4/2009 |
| WO | WO 2009114815 A1 | * | 9/2009 |
| WO | WO 2009132287 A2 | * | 10/2009 |
| WO | WO 2011032181 A2 | * | 3/2011 |

OTHER PUBLICATIONS

Measley et al "Aggregation of the Amphipathic Peptides (AAKA)n into Antiparallel B-sheets" JACS 128:13324-13325. Published online Sep. 27, 2006.*
Measey T and Schweitzer-Stenner R "Aggregation of the Amphipathic Peptides (AAKA)n into Antiparallel B-sheets" JACS 128:13324-13325. Published online Sep. 27, 2006.*
Anonymous "Technical Information: N-Terminal Acetylation and C-terminal Amidation of Peptides" Thermo Electron Corporation Brochure. Published 2004.*
Pak et al "Binding effect and design of a competitive inhibitory peptide for HMG-CoA reductase through modeling of an active peptide backbone" Bioorgan & Med Chem 16:1309-1318. Published Oct. 23, 2007.*
Chao et al "Binding of uracil derivative to hydrophobic peptides and sodium dodecyl sulfate" J Biol Chem 251:6924-6928. Published 1976.*

(Continued)

*Primary Examiner* — James H Alstrum Acevedo
*Assistant Examiner* — Zachary J Miknis
(74) *Attorney, Agent, or Firm* — Choate, Hall & Stewart LLP; Charles E. Lyon; Kevin M. Henry

(57) ABSTRACT

The present invention provides an amphiphilic linear peptide and/or peptoid as well as a hydrogel that includes the amphiphilic linear peptide/peptoid. The amphiphilic linear peptide/peptoid is capable of forming a hydrogel. These peptides/peptoids include short amphiphilic sequences with a hydrophobic portion of aliphatic amino acids and at least one acidic, neutral, or basic polar amino acid. The amphiphilic linear peptide/peptoid is build up of non repetitive aliphatic amino acids, which may be in the L- or D-form. A plurality of such peptides/peptoids assembles to supramolecular helical fibers and forms peptide hydrogels after assembly. A corresponding hydrogel is formed in aqueous solutions at physiological pH and is thus useful for inter alia cell culture, tissue engineering, and drug release. Such hydrogels which are rigid, biocompatible and entrapping up to 99.9% of water are also well suited for applications utilizing electronic devices.

24 Claims, 26 Drawing Sheets

(56) References Cited

OTHER PUBLICATIONS

International Search Report for PCT/SG2010/000469, 8 pages (Mar. 23, 2011).

Koda, D. et al., Proteinase-mediated drastic morphological change of peptide-amphiphile to induce supramolecular hydrogelation, Chemical Communications, 46:979-981 (2010).

Measey, T. J. et al., Aggregation of the Amphipathic Peptides $(AAKA)_n$ into Antiparallel β-Sheets, Journal of the American Chemical Society, 128:13324-13325 (2006).

Written Opinion for PCT/SG2010/000469, 10 pages (Mar. 23, 2011).

Yu-Lin, S. et al., Two-dimensional differentiation of neural stem cells induced by self-assembled hydrogel from IKVAV-containing peptide amphiphile, Journal of Clinical Rehabilitative Tissue Engineering Research, 13(34):6667-6670 (2009) (English Abstract).

Yulin, S. et al., Angiogenesis Induced with Neotype Amphiphic Peptide, Journal of Biomedical Engineering, 27(1):113-115 (2010) (English Abstract).

\* cited by examiner

Fig. 1A: SEVEN MEMBER PEPTIDES WITH ASPARTIC ACID HEAD GROUP

| SEQID No. | Peptide | Peptide sequence | Observation |
|---|---|---|---|
| 1 | Ac-LD$_7$ (L) | Ac-LIVAGDD-COOH (L) | Hydrogelation |

Fig. 1B: SIX MEMBER PEPTIDES WITH ASPARTIC ACID HEAD GROUP

| SEQID No. | Peptide | Peptide sequence | Observation |
|---|---|---|---|
| 2 | Ac-LD$_6$ (L Form) | Ac-LIVAGD-COOH (L) | Hydrogelation |
| 3 | Ac-LD$_6$ (D Form) | Ac-LIVAGD-COOH (D) | Hydrogelation |
| 4 | Ac-AD$_6$(L) | Ac-AIVAGD-COOH (L) | Hydrogelation |
| 5 | Ac-AD$_6$(D) | Ac-AIVAGD-COOH (D) | Hydrogelation |
| 6 | Ac-ID$_6$ (L) | Ac-ILVAGD-COOH (L) | Hydrogelation |
| 7 | Ac-ID$_6$ (D) | Ac-ILVAGD-COOH (D) | Hydrogelation |
| 8 | Ac-LD$_{6-1}$(L Form) | Ac-LAVAGD-COOH (L) | Hydrogelation |
| 9 | Ac-LD$_{6-2}$ (L Form) | Ac-LIVAAD-COOH (L) | Hydrogelation |

Fig. 1C: SIX MEMBER PEPTIDES WITH SERINE HEAD GROUP

| SEQID No. | Peptide | Peptide sequence | Observation |
|---|---|---|---|
| 10 | Ac-LS$_6$ (L) | Ac-LIVAGS-COOH (L) | Hydrogelation |
| 11 | Ac-LS$_6$ (D) | Ac-LIVAGS-COOH (D) | Hydrogelation |
| 12 | Ac-AS$_6$(L) | Ac-AIVAGS-COOH (L) | Hydrogelation |
| 13 | Ac-IS$_6$ (L) | Ac-ILVAGS-COOH (L) | Hydrogelation |

Fig. 1D: SIX MEMBER PEPTIDES WITH THREONINE HEAD GROUP

| SEQID No. | Peptide | Peptide sequence | Observation |
|---|---|---|---|
| 14 | Ac-LT$_6$ (L) | Ac-LIVAGT-COOH (L) | Hydrogelation |
| 15 | Ac-AT$_6$ (L) | Ac-AIVAGT-COOH (L) | Hydrogelation |

Fig. 1E: SEVEN MEMBER PEPTIDES WITH GLUTAMIC ACID HEAD GROUP

| SEQID No. | Peptide | Peptide sequence | Observation |
|---|---|---|---|
| 16 | Ac-LE$_7$ (L) | Ac-LIVAGEE-COOH (L) | Hydrogelation |

Fig. 1F: SIX MEMBER PEPTIDES WITH GLUTAMIC ACID HEAD GROUP

| SEQID No. | Peptide | Peptide sequence | Observation |
|---|---|---|---|
| 17 | Ac-LE$_6$ (L Form) | Ac-LIVAGE-COOH (L) | Hydrogelation |
| 18 | Ac-LE$_6$ (D Form) | Ac-LIVAGE-COOH (D) | Hydrogelation |

Fig. 1G: SIX MEMBER PEPTIDES WITH LYSINE HEAD GROUP

| SEQID No. | Peptide | Peptide sequence | Observation |
|---|---|---|---|
| 19 | Ac-LK$_6$ (L Form) | Ac-LIVAGK-CONH$_2$ (L) | Hydrogelation |

Fig. 1H: FIVE MEMBER PEPTIDES WITH ASPARTIC ACID HEAD GROUP

| SEQID No. | Peptide | Peptide sequence | Observation |
|---|---|---|---|
| 20 | Ac-LD$_{5-1}$(L) | Ac-LIVAD-COOH (L) | Hydrogelation |
| 21 | Ac-LD$_{5-2}$ (L) | Ac-LIVGD-COOH (L) | Hydrogelation |

Fig. 1I: FOUR MEMBER PEPTIDES WITH ASPARTIC ACID HEAD GROUP

| SEQID No. | Peptide | Peptide sequence | Observation |
|---|---|---|---|
| 22 | Ac-ID$_4$(L) | Ac-IVAD-COOH (L) | Hydrogelation |
| 23 | Ac-ID$_4$(D) | Ac-IVAD-COOH (D) | Hydrogelation |

Fig. 1J: THREE MEMBER PEPTIDES WITH ASPARTIC ACID HEAD GROUP

| SEQID No. | Peptide | Peptide sequence | Observation |
|---|---|---|---|
| 24 | Ac-ID$_3$(L) | Ac-IVD-COOH (L) | Hydrogelation | a. Ac-LD-6 (L) 1mg/ml b. Ac-AD-6 (L) 5mg/ml a. Ac-AS-6 (L) 5mg/ml b. Ac-AS-6 (L) 10mg/ml c. Ac-AS-6 (L) 15mg/ml

ESEM image of ACLD6 (L) gels at magnification of 260X at 4 °C.

ESEM image of ACLD6 (L) gels at magnification of 1000X at 4 °C.

ESEM image of ACLD6 (L) gels at magnification of 2000X at 4 °C.

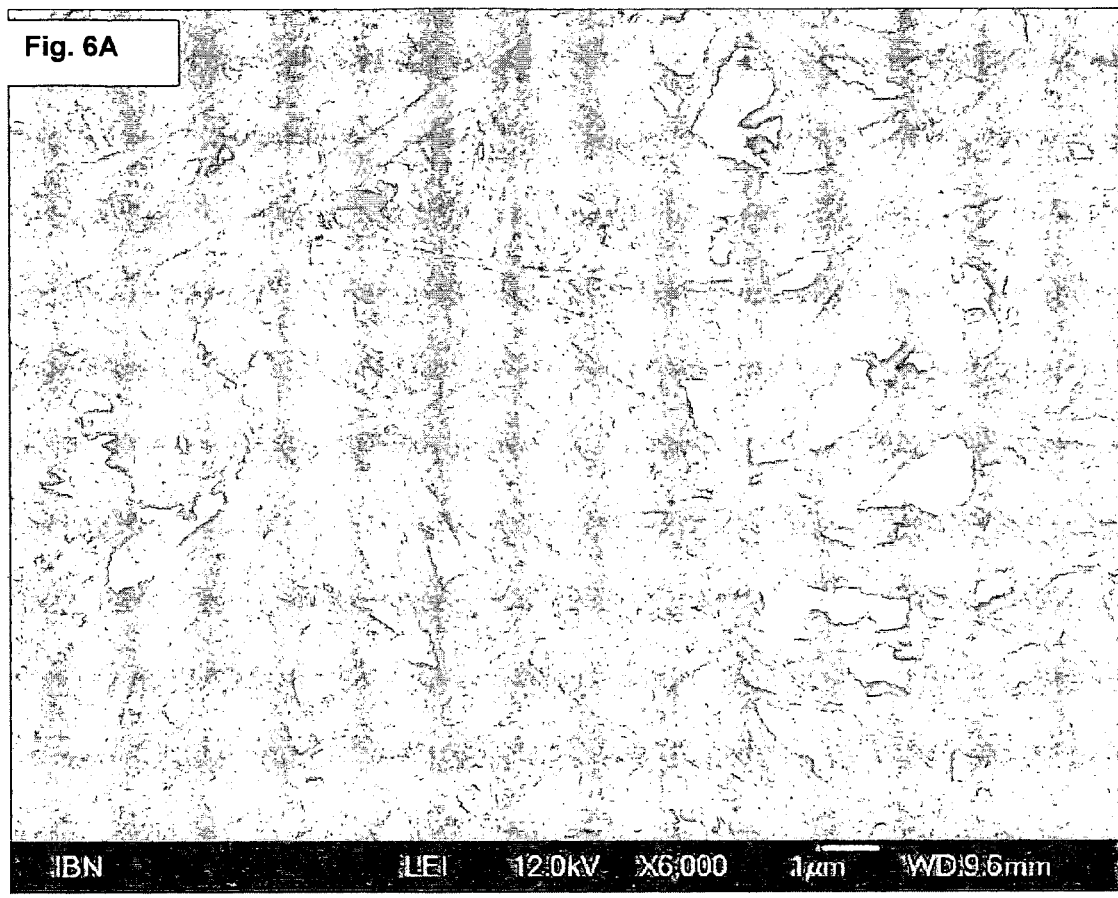

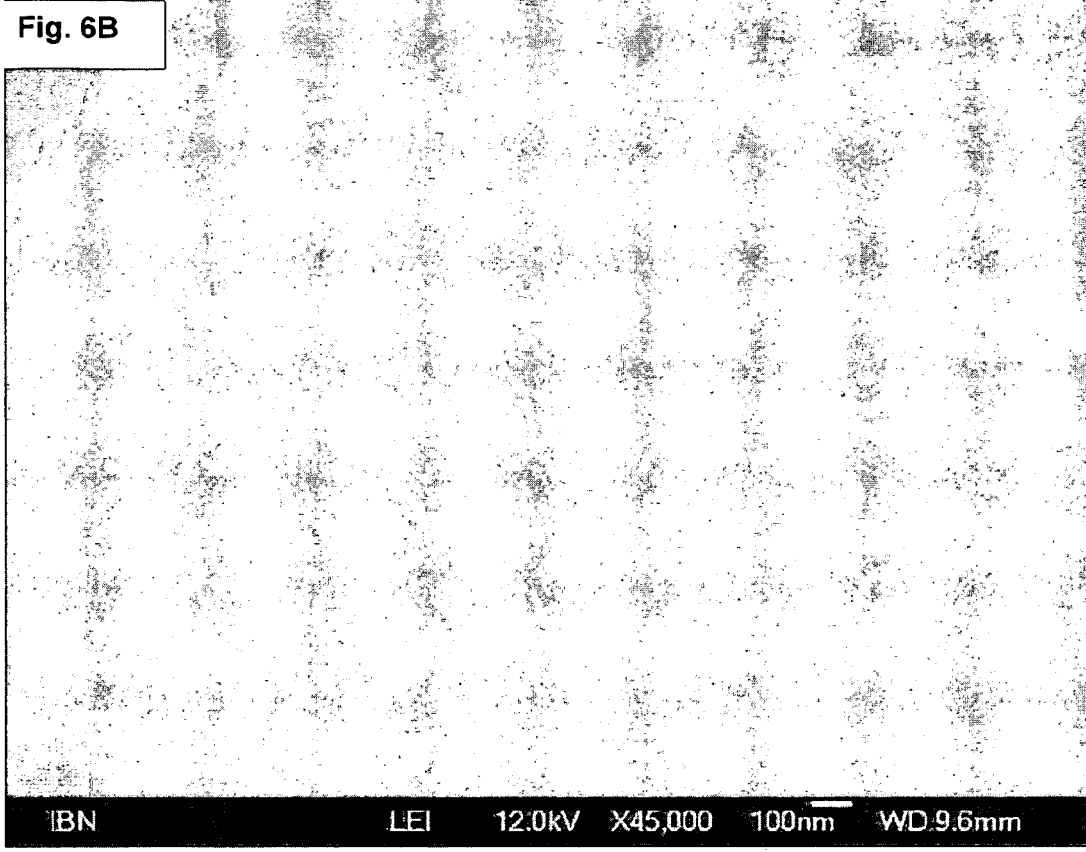

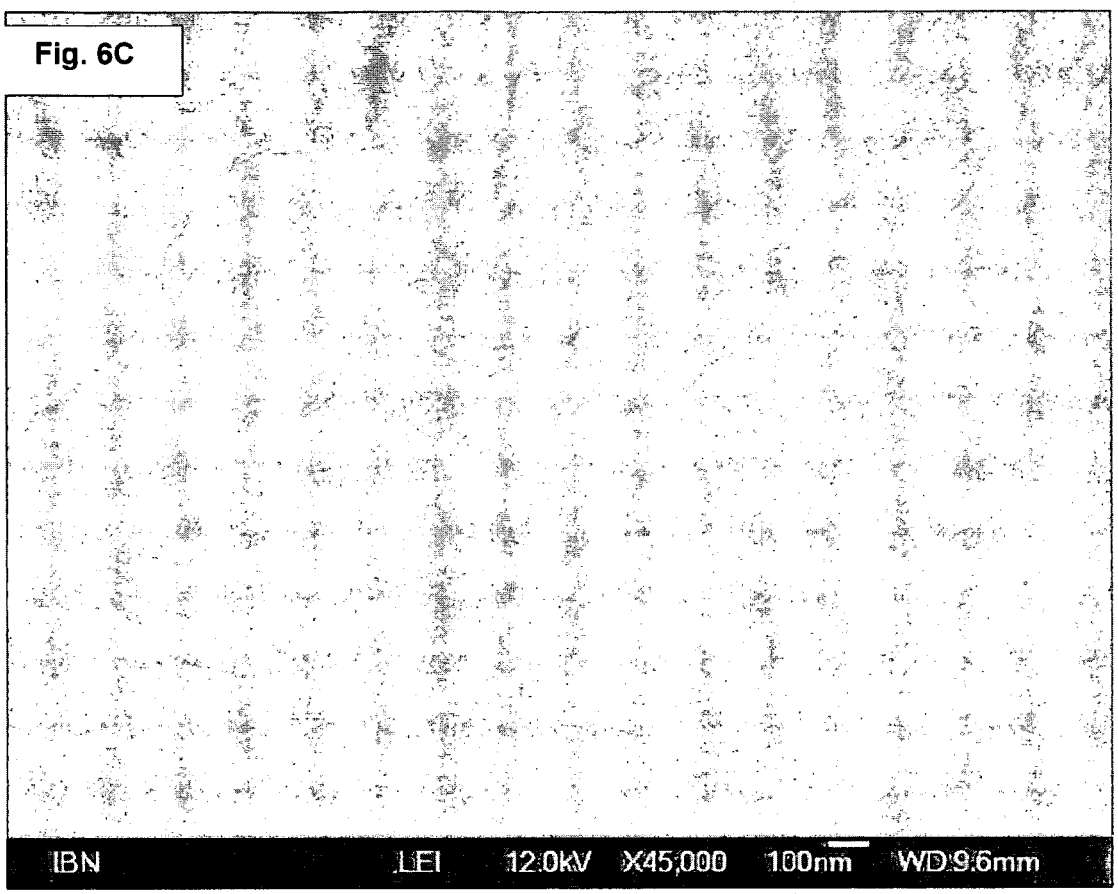

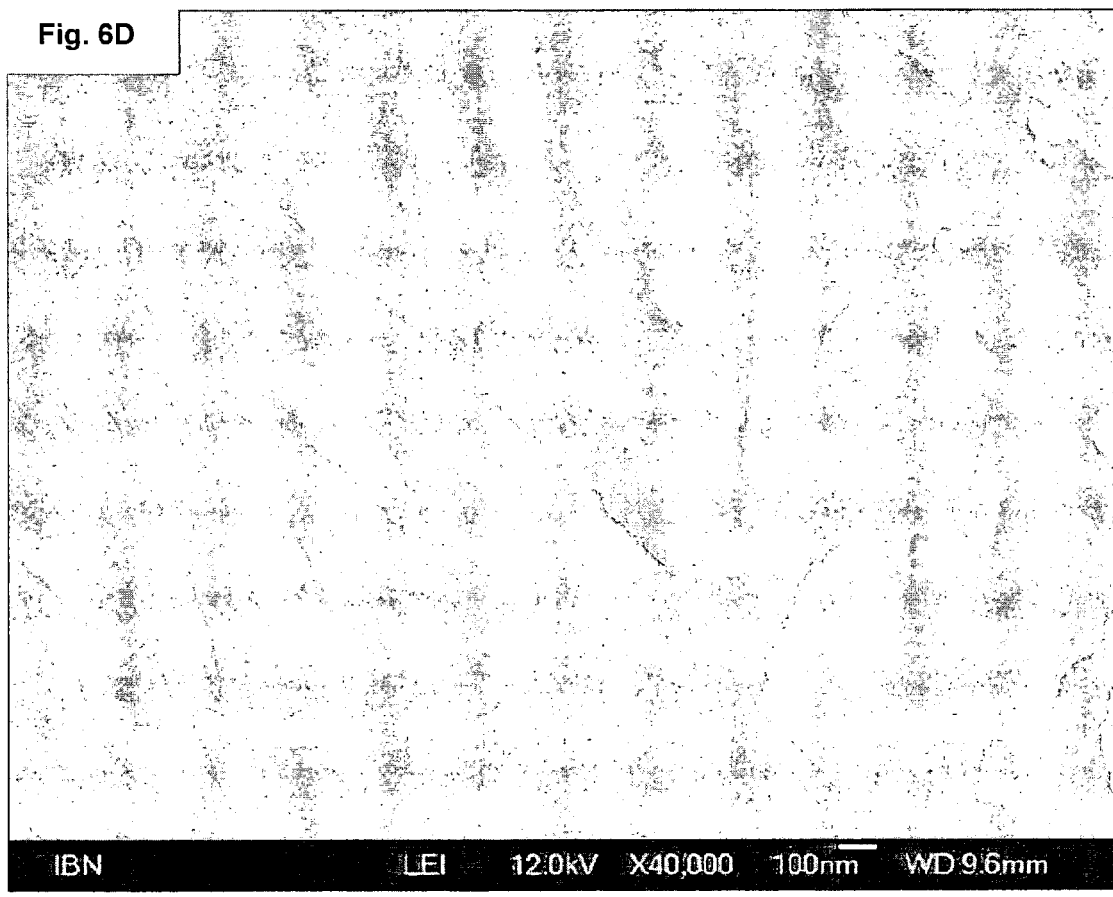

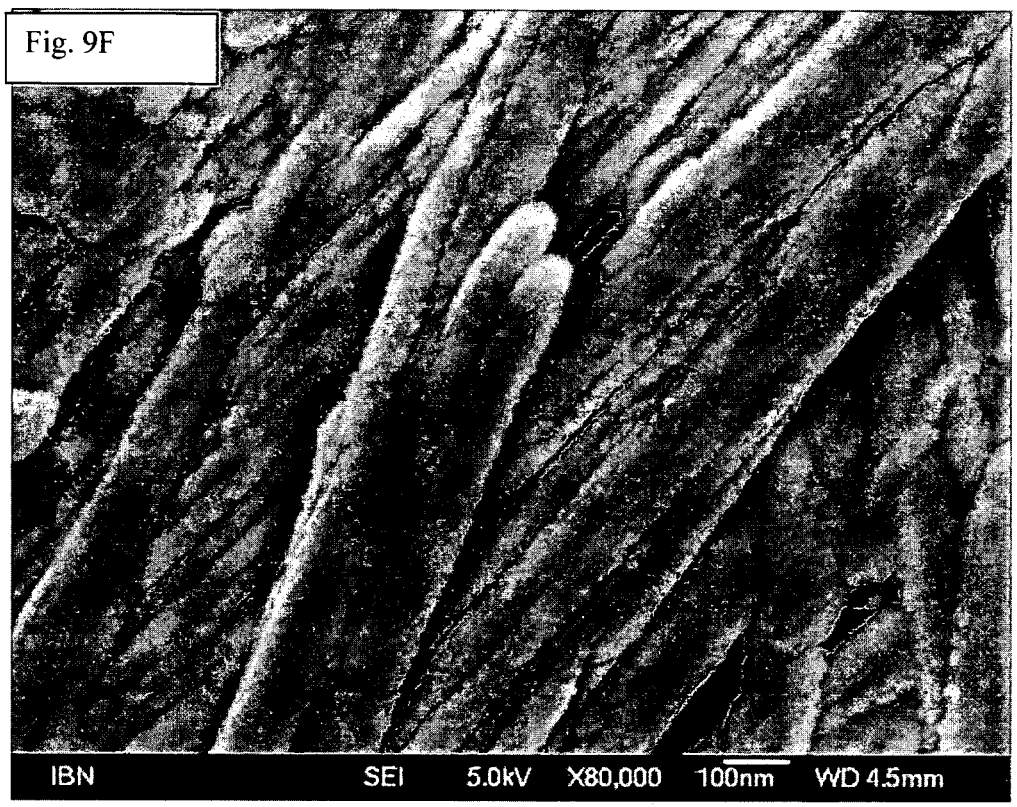

| Gelatin concentration | Frequency [rad/s] | Storage Modulus [Pa] | Loss Modulus [Pa] |
|---|---|---|---|
| 10 mg/ml | 0.1 | 17.63 | 2.77 |
| 15 mg/ml | | 36.72 | 5.48 |
| 20 mg/ml | | 54.36 | 3.95 |
| 10 mg/ml | 1 | 20.87 | 0.80 |
| 15 mg/ml | | 50.68 | 5.93 |
| 20 mg/ml | | 57.00 | 6.95 |
| 10 mg/ml | 10 | 21.90 | 0.86 |
| 15 mg/ml | | 74.35 | -15.48 |
| 20 mg/ml | | 62.63 | -7.27 |
| 10 mg/ml | 100 | 21.68 | 3.83 |
| 15 mg/ml | | 56.35 | 8.74 |
| 20 mg/ml | | 73.80 | 10.60 | the development of molecular electronic devices (A. R. Hirst et al. Angew. Chem. Int. Ed., 47, 8002-8018, 2008)

AMPHIPHILIC LINEAR PEPTIDE/PEPTOID AND HYDROGEL COMPRISING THE SAME

SEQUENCE LISTING

In accordance with 37 CFR §1.52(e)(5), a Sequence Listing in the form of a text file (entitled "Supplemental Sequence Listing C.txt," created on Jan. 7, 2015, and 19 KB in size) is incorporated herein by reference in its entirety.

FIELD OF THE INVENTION

The present invention provides an amphiphilic linear peptide and/or peptoid as well as a hydrogel that includes the amphiphilic linear peptide/peptoid. The amphiphilic linear peptide/peptoid is capable of forming a hydrogel. These peptides/peptoids include short amphiphilic sequences with a hydrophobic portion of aliphatic amino acids and at least one acidic, neutral, or basic polar amino acid. The amphiphilic linear peptide/peptoid is build up of non repetitive aliphatic amino acids, which may be in the L- or D-form. A plurality of such peptides/peptoids assembles to supramolecular helical fibers and forms peptide hydrogels after assembly. A corresponding hydrogel is formed in aqueous solutions at physiological pH and is thus useful for inter alia cell culture, tissue engineering, and drug release. Such hydrogels which are rigid, biocompatible and entrapping up to 99.9% of water are also well suited for applications utilizing electronic devices.

BACKGROUND OF THE INVENTION

Supramolecular structures are held together by intermolecular bondings that are responsible for the organization of polymolecular systems. The non-covalent, intermolecular forces which are required for the assembly of the defined supramolecular structures are mainly electrostatic interactions, hydrogen bondings, van der Waals forces, etc. Supramolecular chemistry or biology gathers a vast body of two or three dimensional complex structures and entities formed by association of chemical or biological species. These associations are governed by the principles of molecular complementarity or molecular recognition and self-assembly. The knowledge of the rules of intermolecular association can be used to design polymolecular assemblies in form of membranes, films, layers, micelles, tubules, gels for a variety of biomedical or technological applications (J.-M. Lehn, Science, 295, 2400-2403, 2002).

Peptides have been used for the fabrication of supramolecular structures through molecular self-assembly (S. Zhang, Nature Biotechnology, 21, 1171-1178, 2003). Peptides are for instance able to assemble into nanotubes (U.S. Pat. No. 7,179,784) or into supramolecular hydrogels consisting of three dimensional scaffolds with a large amount of around 98-99% immobilized water or aqueous solution. The peptide-based biomaterials are powerful tools for potential applications in biotechnology, medicine and even technical applications. Depending on the individual properties these peptide-based hydrogels are thought to serve in the development of new materials for tissue engineering, regenerative medicine, as drug delivery vehicles or as peptide chips for pharmaceutical research and diagnosis (E. Place et al., Nature Materials, 8, 457-470, 2009). There is also a strong interest to use peptide-based self-assembled biomaterial such as gels for the development of molecular electronic devices (A. R. Hirst et al. Angew. Chem. Int. Ed., 47, 8002-8018, 2008)

A variety of "smart peptide hydrogels" have been generated that react on external manipulations such as temperature, pH, mechanical influences or other stimuli with a dynamic behavior of swelling, shrinking or decomposing. Nevertheless, these biomaterials are still not "advanced" enough to mimic the biological variability of natural tissues as for example the extracellular matrix (ECM) or cartilage tissue or others. The challenge for a meaningful use of peptide hydrogels is to mimic the replacing natural tissues not only as "space filler" or mechanical scaffold, but to understand and cope with the biochemical signals and physiological requirements that keep the containing cells in the right place and under "in vivo" conditions (R. Fairman and K. Akerfeldt, Current Opinion in Structural Biology, 15, 453-463, 2005).

Much effort has been undertaken to understand and control the relationship between peptide sequence and structure for a rational design of suitable hydrogels. In general hydrogels contain macroscopic structures such as fibers that entangle and form meshes. Most of the peptide-based hydrogels utilize as their building blocks β-pleated sheets which assemble to fibers. Later it was shown that it is possible to design hydrogelating self-assembling fibers purely from α-helices. Besides β-sheet structure-based materials (S. Zhang et al., PNAS, 90, 3334-3338, 1993: A. Aggeli et al., Nature, 386, 259-262, 1997, etc.) a variety of α-helical hydrogels has been developed (W. A. Petka et al., Science, 281, 389-392, 1998; C. Wang et al., Nature, 397, 417-420, 1999; C. Gribbon et al., Biochemistry, 47, 10365-10371, 2008; E. Banwell et al., Nature Materials, 8, 596-600, 2009, etc.).

Nevertheless, the currently known peptide hydrogels are in most of the cases associated with low rigidity, sometimes unfavorable physiological properties and/or complexity and the requirement of substantial processing thereof which leads to high production costs. There is therefore a widely recognized need for peptide hydrogels that are easily formed, nontoxic and have a sufficiently high rigidity for standard applications.

SUMMARY OF THE INVENTION

It is therefore desirable to provide a biocompatible compound that is capable of forming a hydrogel that meets at least some of the above requirements to a higher extent than currently available hydrogels and that is not restricted by the above mentioned limitations.

The objects of the present invention are solved by an amphiphilic peptide and/or peptoid capable of forming a hydrogel, the amphiphilic peptide and/or peptoid comprising an amphiphilic sequence consisting of:
  a hydrophobic sequence stretch of n aliphatic amino acids, wherein n is an integer from 2 to 15, and
  a hydrophilic sequence stretch linked to said hydrophobic sequence stretch and having a polar moiety which is acidic, neutral or basic, said polar moiety comprising in adjacent hydrophilic amino acids, wherein m is an integer from 1 to 5.

In one embodiment the amphiphilic peptide and/or peptoid has a C-terminus and an N-terminus wherein the N-terminus is protected by a protecting group, wherein said protecting group preferably is an acetyl group.

In one embodiment, the amphiphilic peptide and/or peptoid has a C-terminus, which, if a basic polar amino acid is located at the C-terminus, is preferably amidated.

In one embodiment, n is an integer from 2 to 6.

In one embodiment, m is an integer from 1 to 2.

In one embodiment, the amphiphilic peptide and/or peptoid consists of o amphiphilic sequences, as defined above, which amphiphilic sequences are linked to each other, o being an integer from 1 to 50.

In one embodiment, for a given amphiphilic peptide and/or peptoid, said aliphatic amino acids and said hydrophilic amino acids are either D-amino acids or L-amino acids.

In one embodiment, each of the hydrophilic amino acids has a polar group which is independently selected from a hydroxyl, an ether, a carboxyl, an imido, an amido, an ester, an amino, a guanidino, a thio, a thioether, a seleno, and a telluro group.

In one embodiment, said polar moiety of said hydrophilic sequence stretch comprises m adjacent hydrophilic amino acids, m being defined as defined above, said hydrophilic amino acids being selected from the group comprising aspartic acid, asparagine, glutamic acid, glutamine, 5-N-ethyl-glutamine (theanine), citrulline, thio-citrulline, cysteine, homocysteine, methionines ethionine, selenomethionine, telluromethionine, threonine, allo-threonine, serine, homoserine, arginine, homoarginine, ornithine, lysine and N(6)-carboxymethyllysine, histidine, and wherein said hydrophobic sequence stretch comprises n aliphatic amino acids, n being as defined above, said aliphatic amino acids being selected from the group comprising isoleucine, norleucine, leucine, valine, alanine, glycine, homoallylglycine and homopropargylglycine.

In one embodiment, m is 1 to 2.

In one embodiment, m is 2 and said polar moiety comprises two identical amino acids, or m is 1 and said polar moiety comprises any one of aspartic acid, asparagine, glutamic acid, glutamine, serine, threonine, cysteine, methionine, lysine and histidine.

In one embodiment, said polar moiety is adjacent to the hydrophobic sequence stretch of n aliphatic amino acids.

In one embodiment, said polar moiety has a sequence selected from Asp, Asn, Glu, Gln, Ser, Thr, Cys, Met, Lys, His, Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gln, Asp-Asn, Asn-Asp Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu.

In one embodiment, said polar moiety comprises the C-terminus of the amphiphilic peptide and/or peptoid, or wherein said polar moiety comprises the N-terminus of the amphiphilic peptide and/or peptoid.

In one embodiment, both said C-terminus and said N-terminus do not carry any protecting groups attached to them.

In one embodiment, said polar, moiety comprises the C-terminus of the amphiphilic peptide and/or peptoid, wherein both said C-terminus and said N-terminus do not carry any protecting groups attached to them.

In one embodiment, said polar moiety comprises the C-terminus of the amphiphilic peptide and/or peptoid, wherein said C-terminus does not carry any protecting group, and wherein said N-terminus carries a protecting group.

In one embodiment, said protecting group is an acetyl group attached to the amino-group of said N-terminus.

In one embodiment, said polar moiety comprises the C-terminus of the amphiphilic peptide and/or peptoid, wherein said C-terminus carries a protecting group, and wherein said N-terminus does not carry any protecting group.

In one embodiment, said protecting group is an amido-group attached to the carboxyl group of said C-terminus.

In one embodiment, said polar moiety comprises the C-terminus of the amphiphilic peptide and/or peptoid, wherein both said C-terminus and N-terminus carry a protecting group.

In one embodiment, said C-terminus protecting group is an amido-group attached to the carboxyl group of said C-terminus, and wherein said N-terminus protecting group is an acetyl group attached to the amino-group of said N-terminus.

In one embodiment, said polar moiety consists of at least one amino acid positioned at the C-terminus of the amphiphilic peptide and/or peptoid.

In one embodiment, said hydrophobic sequence stretch comprises and/or forms the N-terminus of the amphiphilic peptide and/or peptoid.

In one embodiment, all or a portion of the aliphatic amino acids of the hydrophobic sequence stretch are arranged in an order of decreasing amino acid size in the direction from N- to C-terminus of the amphiphilic peptide and/or peptoid, wherein the size of the aliphatic amino acids is defined as I=L>V>A>G.

In one embodiment, said aliphatic amino acids arranged in an order of decreasing amino acid size have a sequence which is a repetitive or non-repetitive sequence.

In one embodiment, said aliphatic amino acids arranged in order of decreasing amino acid size have a sequence with a length of 2 to 7, preferably 2 to 6, more preferably 2 to 5 amino acids.

In one embodiment, said aliphatic amino acids arranged in an order of decreasing amino acid size have a sequence selected from LIVAG, ILVAG, LIVAA, LAVAG, WAG, LIVA, LIVG, IVA and IV, wherein, optionally, there is an A preceding such sequence at the N-terminus.

In one embodiment, all or a portion of the aliphatic amino acids of the hydrophobic sequence stretch are arranged in an order of identical amino acid size in the amphiphilic peptide and/or peptoid.

In one embodiment, said aliphatic amino acids arranged in order of identical amino acid size have a sequence with a length of 2 to 4 amino acids.

In one embodiment, said aliphatic amino acids arranged in an order of identical size have a sequence selected from LLLL, LLL, LL, IIII, III, II, VVVV, VVV, VV, AAAA, AAA, AA, GGGG, GGG, and GG.

In one embodiment, the amphiphilic sequence undergoes a conformational change during self-assembly, preferably a conformational change from a random coil conformation to a helical intermediate structure to a final beta conformation.

In one embodiment, the conformational change is concentration dependent.

In one embodiment, the amphiphilic linear sequence comprises a single hydrophilic and at least two aliphatic amino acids.

In one embodiment, the amphiphilic sequence is one of SEQ ID NO: 1-42.

It should be noted that any of the amphiphilic sequences may carry a protecting group at the N-terminus or the C-terminus or both. For example, SEQ ID NO:1-42 may all carry an acetyl group as protecting group at the N-terminus. As a further example, SEQ ID NO: 19 (LIVAGK) may carry an amido-group as protecting group at the C-terminus, and additionally it may have an acetyl group at the N-terminus as protecting group.

In one embodiment, said amphiphilic peptide and/or peptoid is stable in aqueous solution at physiological conditions at ambient temperature for a period of time in the range from 1 day to at least 6 months, preferably to at least 8 months more preferably to at least 12 months.

In one embodiment, the amphiphilic peptide and/or peptoid is stable in aqueous solution at physiological conditions, at a temperature up to 90° C., for at least 1 hour.

The objects of the present invention are solved by a hydrogel comprising the amphiphilic peptide and/or peptoid according to the present invention.

In one embodiment, the hydrogel is stable in aqueous solution at ambient temperature for a period of at least 7 days, preferably at least 2 to 4 weeks, more preferably at least 1 to 6 months.

In one embodiment, the hydrogel is characterized by a storage modulus G' to loss modulus G" ratio that is greater than 2.

In one embodiment, the hydrogel is characterized by a storage modulus G' from 100 Pa to 80,000 Pa at a frequency in the range of from 0.02 Hz to 16 Hz.

In one embodiment, the hydrogel has a higher mechanical strength than collagen or its hydrolyzed form (gelatin).

In one embodiment, the hydrogel according to the present invention comprises fibers of the amphiphilic peptide and/or peptoid as defined above, said fibers defining a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound.

In one embodiment, the hydrogel comprises at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer.

In one embodiment, the fibers of the amphiphilic polymer are coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer.

In one embodiment, the hydrogel is comprised in at least one of a fuel cell, a solar cell, an electronic cell, a biosensing device, a medical device, an implant, a pharmaceutical composition and a cosmetic composition.

In one embodiment, the hydrogel according to the present invention is for use in at least one of the following: release of a pharmaceutically active compound, medical tool kit, a fuel cell, a solar cell, an electronic cell, tissue regeneration, stem cell therapy and gene therapy.

In one embodiment, the hydrogel according to the present invention is injectable.

The objects of the present invention are solved by a method of preparing a hydrogel, the method comprising dissolving an amphiphilic peptide and/or peptoid according to the present invention in an aqueous solution.

In one embodiment, the dissolved amphiphilic peptide and/or peptoid in aqueous solution is further exposed to temperature, wherein the temperature is in the range from 20° C. to 90° C., preferably from 20° C. to 70° C.

In one embodiment, the amphiphilic peptide and/or peptoid is dissolved at a concentration from 0.01 µg/ml to 100 mg/ml, preferably at a concentration from 1 mg/ml to 50 mg/ml, more preferably at a concentration from about 1 mg/ml to about 20 mg/ml.

The objects of the present invention are also solved by a surgical implant, or stent, the surgical implant or stent comprising a peptide and/or peptoid scaffold, wherein the peptide and/or peptoid scaffold is formed by a hydrogel according to the present invention.

The objects of the present invention are also solved by a pharmaceutical and/or cosmetic composition and/or a biomedical device and/or electronic device comprising the amphiphilic peptide and/or peptoid according to the present invention.

In one embodiment, the pharmaceutical and/or cosmetic composition and/or the biomedical device, and/or the electronic devices as defined above, further comprises a pharmaceutically active compound.

In one embodiment, the pharmaceutical and/or cosmetic composition as defined above, further comprises a pharmaceutically acceptable carrier.

The objects of the present invention are also solved by a kit of parts, the kit comprising a first container with an amphiphilic peptide and/or peptoid according to the present invention and a second container with an aqueous solution.

In one embodiment, the aqueous solution of the second container further comprises a pharmaceutically active compound.

In one embodiment, the first container with an amphiphilic peptide and/or peptoid further comprises a pharmaceutically active compound.

The objects of the present invention are solved by a method of tissue regeneration comprising the steps:
  providing a hydrogel as defined above,
  exposing said hydrogel to cells which are to form regenerated tissue,
  allowing said cells to grow on said hydrogel.

In one embodiment, the method as defined above is performed in-vitro or in-vivo.

In one embodiment, the method as defined above is performed in vivo, wherein, in step a), said hydrogel is provided at a place in a body where tissue regeneration is intended.

In one embodiment, said step a) is performed by injecting said hydrogel at a place in the body where tissue regeneration is intended.

In a first aspect the present invention provides an amphiphilic peptide and/or peptoid capable of forming a hydrogel. The amphiphilic peptide and/or peptoid includes a hydrophobic and a hydrophilic sequence. This hydrophobic sequence has a length of n L- or D-amino acids. n is an integer, which may typically range from 2 to about 15. The hydrophilic sequence has a polar and/or charged moiety comprising m L- or D-amino acids. m is an integer from 1 to 5. Each of the m aliphatic amino acids carries an independently selected polar group. The amphiphilic linear sequence has a net charge at physiological pH and a N-terminus carrying a protecting group. The protecting group can be an acetyl group. The amphiphilic peptide and/or peptoid may comprise o linked amphiphilic peptide and/or peptoid sequences of n hydrophobic and m hydrophilic L- and D-amino acids, wherein o is an integer from 1 to about 50. The amphiphilic peptide and/or peptoid may consist of o linked amphiphilic peptide and/or peptoid sequences of n hydrophobic and m hydrophilic L- and D-amino acids. The value of n may be an integer from 2 to about 15. The value of m may be 1 to 5. The charged and/or polar group of each of the m hydrophilic L- and D-amino acids may be independently selected from a hydroxyl, an ether, a carboxyl, an amido, an ester, an amino, a guanidino, a thio, a thioether, a seleno, and a telluro group. The charged or polar moiety of the hydrophilic sequence may comprise m L- or D-amino acids selected from the group consisting of aspartic acid, asparagine, glutamic acid, glutamine, 5-N-ethyl-glutamine (theanine), citrulline, thiocitrulline, cysteine, homocysteine, methionine, ethionine, selenomethionine, telluromethionine, threonine, allo-threonine, serine, homoserine, arginine, homoarginine, ornithine, lysin and N(6)-carboxymethyllysine. The charged and/or polar moiety of the hydrophilic sequence may comprise two identical amino acids. The two identical amino acids may be adjacent to the non-polar hydrophobic moiety. The charged and/or polar moiety may consist of two amino acids with a sequence selected from Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gin, Asp-Asn, Asn-Asp, Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu. The charged and/or polar moiety may comprise the C-terminus of the amphiphilic peptide and/or peptoid. The charged and/or polar moiety may comprise (i) the C-terminus, the C-terminus carrying an unprotected C-terminal carboxyl group or (ii) the N-terminus, the N-terminus carrying an unprotected N-terminal amino group. The charged and/or polar moiety may comprise the C-terminus of the amphiphilic peptide and/or peptoid, the C-terminus carrying an unprotected C-terminal carboxyl group and wherein the N-terminus carries a protecting group preferably the acetyl group. The protecting group may be an amido protecting group. The charged and/or polar moiety may consist of at least one amino acid positioned at the C-terminus of the amphiphilic peptide and/or peptoid. The hydrophobic sequence may comprise at least two aliphatic amino acids that is defined by a main chain comprising 1 to about 20 carbon atoms. A portion of the amino acids of the non-polar moiety may be arranged in a general sequence of decreasing size in the direction from N- to C-terminus of the amphiphilic peptide and/or peptoid, and the size of adjacent amino acids of the non-polar moiety may be identical or smaller in the direction of the general sequence of decreasing size. The general sequence of decreasing size may be preferably a non-repetitive sequence. The direction of the general sequence of decreasing size in which adjacent amino acids may be of identical or smaller size may be the direction toward the charged and/or polar moiety of the sequence. The portion of the amino acids arranged in a general sequence of decreasing size may have a length of 2-7, preferably 2-6, more preferably 2, 3, 4, 5 or 6 amino acids. The portion of the amino acids arranged in a general sequence of decreasing size may also have a length of n-m-l amino acids and wherein the portion of the amino acids arranged in the general sequence of decreasing size may be positioned between the remaining non-polar amino acid of the non-polar moiety of n-m amino acids and the polar moiety. The remaining non-polar amino acid of the non-polar moiety of n-m amino acids may define the N-terminus or the C-terminus of the amphiphilic peptide and/or peptoid. The remaining non-polar amino acid of the non-polar moiety of n-m amino acids may be one of alanine, valine and glycine. The amphiphilic linear sequence may undergo a conformational change from a random coil conformation to a helical conformation during self-assembly. The conformational change may be concentration dependent. The non-polar moiety of the amphiphilic linear sequence may comprise at least one L- or D-amino acid selected from the group consisting of glycine, homoallylglycine, homopropargylglycine, alanine, valine, leucine, norleucine and isoleucine. The amphiphilic linear sequence may comprise a single polar and/or charge and a single non-polar moiety. The amphiphilic linear sequence may have a positive or a negative net charge. The net charge may be from about −1 to about −4 or from about +5 to about +1. The net charge may be from about −1 to about −2. The net charge may be −2. The net charge may be +1 or +2 or +5. The amphiphilic peptide and/or peptoid may be stable in aqueous solution at physiological conditions at ambient temperature for a period of time in the range from 1 day to at least 6 months, preferably at least 8 months, more preferably at least 12 months. The amphiphilic peptide and/or peptoid may be stable in aqueous solution at physiological conditions at a temperature to 90° C. for at least 1 hour.

In a second aspect the invention provides a hydrogel. The hydrogel includes an amphiphilic peptide and/or peptoid according to the first aspect. The hydrogel may be stable in aqueous solution at ambient temperature for a period of at least 7 days. The hydrogel may be stable in aqueous solution at ambient temperature for a period of at least 2 to 4 weeks. The hydrogel may be stable in aqueous solution at ambient temperature for a period of at least 1 to 6 months. The hydrogel mechanical property may be characterized by a loss modulus G" to storage modulus G' ratio that is less than 1. The hydrogel may be characterized by magnitude of storage modulus G' greater than loss modulus G" by minimum factor of 1.5. The hydrogel may be characterized by a storage modulus G' of from 100 Pa to 80,000 Pa at a frequency in the range of from 0.02 Hz to 16 Hz. The hydrogel may be characterized by higher storage modulus G' with increase in the concentration of peptide. The hydrogel may have a higher mechanical strength than collagen or hydrolyzed form (gelatin). The hydrogel may comprise fibers of an amphiphilic peptide and/or peptoid described herein. The fibers may define a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound. The hydrogel may comprise at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer. The fibers of the amphiphilic polymer may be coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer. The hydrogel may be comprised in at least one of a fuel cell, a solar cell, a electronic cell, a biosensing device, a medical device, an implant, a pharmaceutical composition, drug delivery system, tissue culture medium, biosensor devices and a cosmetic composition. The hydrogel may be for at least one of release of a pharmaceutically active compound, medical tool kit, a fuel cell, a solar cell, an electronic cell, tissue regeneration, stem cell therapy and gene therapy.

In some embodiments the hydrogel may be used for tissue regeneration, drug release or gene therapy.

In a third aspect the invention provides a method of preparing a hydrogel. The method includes providing an amphiphilic peptide and/or peptoid according to the first aspect. The method further includes dissolving and/or dispersing the amphiphilic peptide and/or peptoid in an aqueous solution. The dissolved/dispersed amphiphilic peptide and/or peptoid in aqueous solution may be further exposed to a temperature. The temperature may be selected in the range from about 20° C. to about 90, preferably from 20° C. to 70° C. The amphiphilic peptide and/or peptoid may be dissolved at a concentration from about 0.01 µg/ml to about 100 mg/ml. The amphiphilic peptide and/or peptoid may be dissolved at a concentration from about 1 mg/ml to about 50 mg/ml. The amphiphilic peptide and/or peptoid may be dissolved and/or dispersed at a concentration from about 1 mg/ml to about 30 mg/ml.

In a fourth aspect the invention provides a surgical implant or stent. The surgical implant or stent includes a peptide and/or peptoid scaffold. The peptide and/or peptoid scaffold is defined by a hydrogel according to the second aspect.

In a fifth aspect the invention provides a pharmaceutical and/or cosmetic composition. The pharmaceutical and/or cosmetic composition includes the amphiphilic peptide and/or peptoid according to the first aspect. The pharmaceutical and/or cosmetic composition may comprise a pharmaceutically active compound. The pharmaceutical and/or cosmetic composition may comprise a pharmaceutically acceptable carrier.

In a sixth aspect the invention provides a kit of parts. The kit includes a first container and a second container. The first container includes a peptide and/or peptoid according to the first aspect. The second container includes an aqueous solution. The aqueous solution of the second container may further comprise a pharmaceutically active compound. The first container with an amphiphilic peptide and/or peptoid may further comprise a pharmaceutically active compound.

Other aspects and features of the present invention will become apparent to those skilled in the art upon review of the following description of specific embodiments of the invention in conjunction with the accompanying figures.

BRIEF DESCRIPTION OF THE DRAWINGS

Embodiments of the invention will now be described by way of example with reference to the accompanying drawings, in which:

FIG. 1A 1J represent a sorted list of some exemplary peptides of the invention capable of forming hydrogels. These peptides are embodiments in which the entire peptide consists of a single linear amphiphilic sequence. Peptides which are forming hydrogels are named with a short code, but their individual sequence is disclosed. The peptides of these examples consist of a sequence of natural amino acids containing 3 to 7 amino acids. The N-terminus is acetylated which removes the charge that would otherwise restrain the amphiphilic character of the peptides.

FIG. 6 shows field emission scanning electron microscopy (FESEM) images of hydrogels of Ac-LD 6 (L) (15 mg/ml), where FIG. 6A-D are images obtained at magnifications of 6000×, 45000×, 45000× and 40000× with HV at 10 KV.

FIG. 12A and FIG. 12B depict oscillatory amplitude sweep studies at temperatures of 25° C. and 50° C. for Ac-AD6(L) and Ac-AD6(D) at a concentration of 20 mg/ml with a constant frequency of [1 rad-s] and a gap of 0.8 mm. The graphs indicate the plot of moduli [Pa] versus strain (%) at temperatures of 25° C. and 50° C. The linear viscoelastic range was observed at 0.07% to 0.2 strain % at temperatures of 25° C. and 50° C. FIG. 12C and FIG. 12D depict oscillatory frequency sweep Studies at temperatures of 25° C. and 50° C. for Ac-AD6(L) and Ac-AD6 (D) at a concentration of 20 mg/ml with varying frequency ranges from 0.1 to 100 [Rad/s] with a constant strain [%] of 0.1% linear viscoelastic range and a gap of 0.8 mm.

FIG. 15 illustrates the biocompatibility of peptide-based hydrogels of the invention using further cell lines.

DETAILED DESCRIPTION OF THE INVENTION

Figure 2:
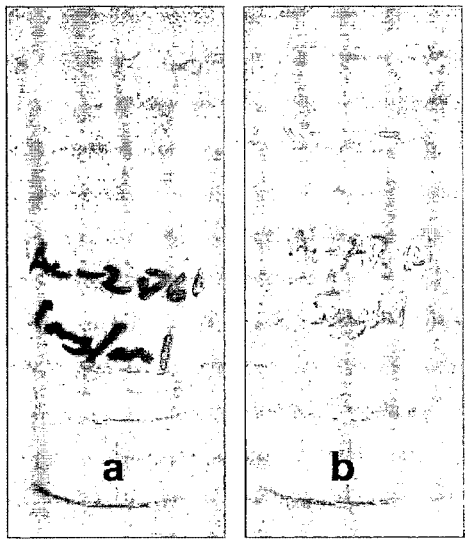
FIG. 2 depicts gelation pictures for peptide based hydrogels at lowest concentrations.
Figure 3:
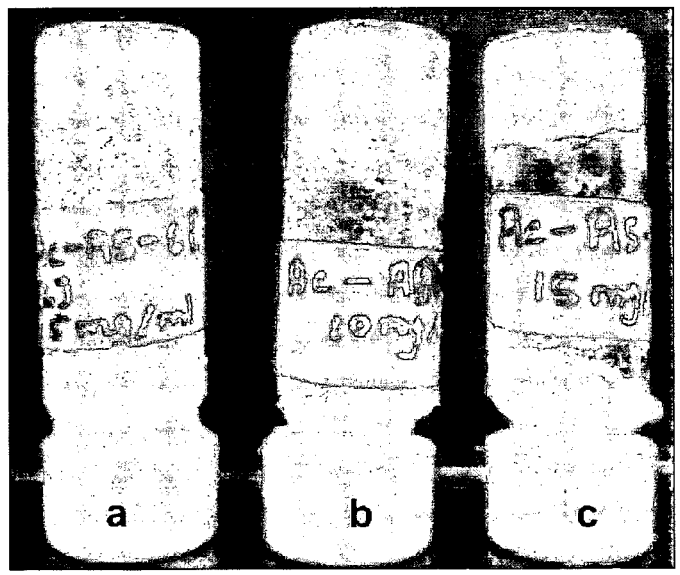
FIG. 3 depicts gelation pictures for Ac-AS-6 (L) at concentrations of 5 mg/ml, 10 mg/ml, 15 mg/ml.
Figure 4:
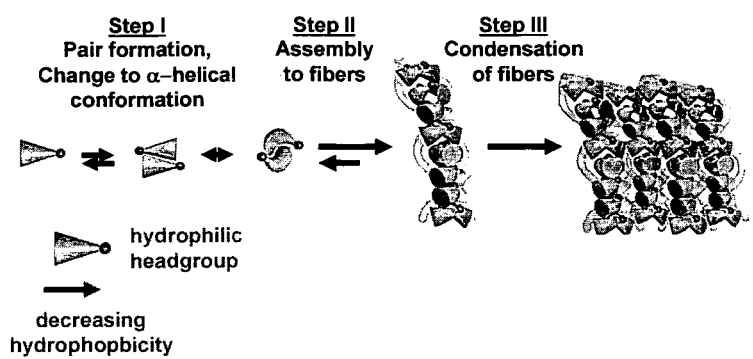
FIG. 4 depicts a hypothesis of self-assembly from peptide monomers to supramolecular network of condensed fibers. (A) Assembly is believed to initiate with antiparallel pairing of two peptide monomers by changing to α-helical conformations. Subsequently, peptide pairs assemble to fibers and nanostructures. Condensation of peptide fibers to fiber aggregates results in hydrogel formation
Figure 5A:
FIG. 5 depicts environmental scanning electron microscopy (ESEM) images of hydrogels of Ac-LD6 (L) (10 mg/ml), where FIG. 5A, FIG. 5B, FIG. 5C, and are images obtained at magnification of 260×, 1000×, 2000×, 2400×, 4000× at a temperature of 4° C. with HV at 10 KV. The images indicate the formation of fibrous structures.
Figure 5B:
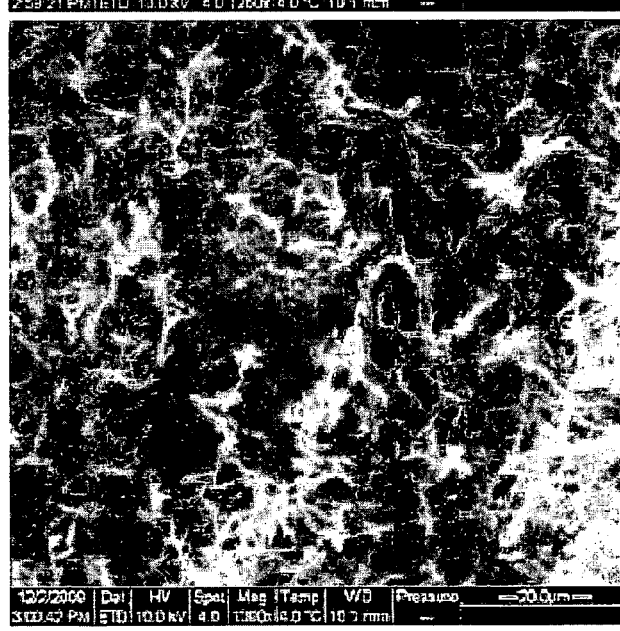
Figure 5C:
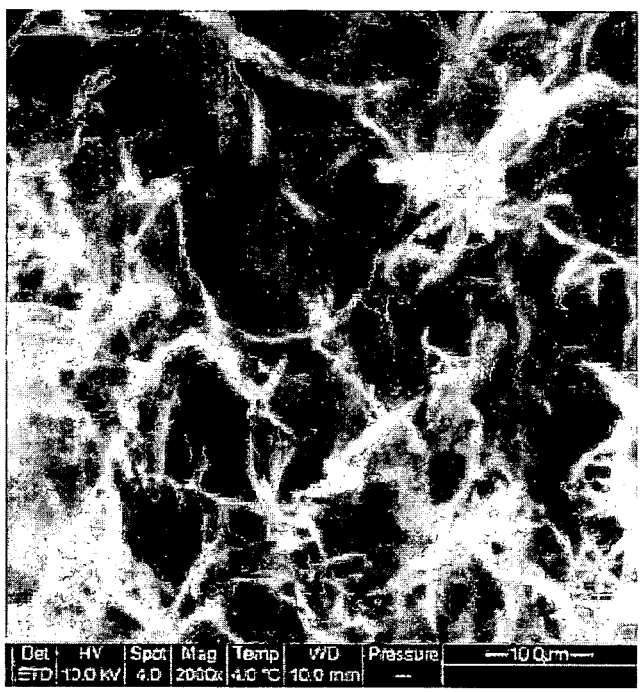
Figure 7A:
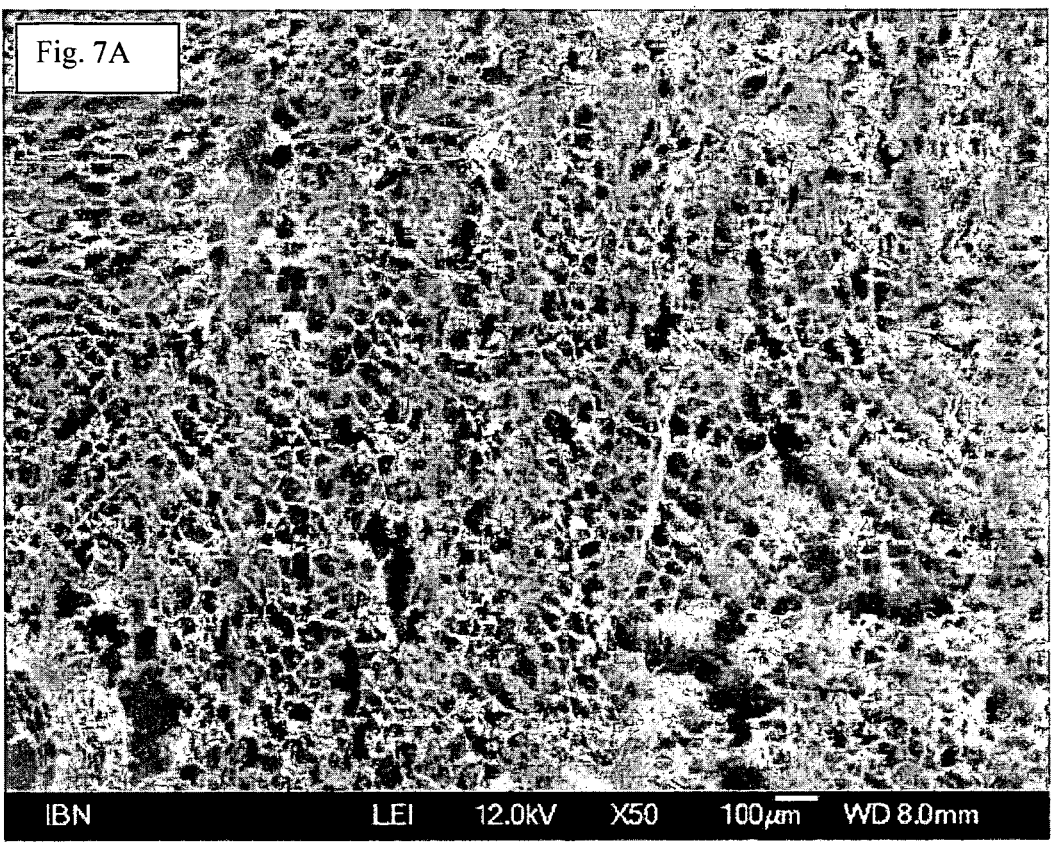
FIG. 7 depicts field emission scanning electron microscopy (FESEM) images of Ac-AD6 (D) hydrogels (20 mg/ml) at a magnification of 50× (FIG. 7A) and 20000× (FIG. 7 B) at 12 KV.
Figure 7B:
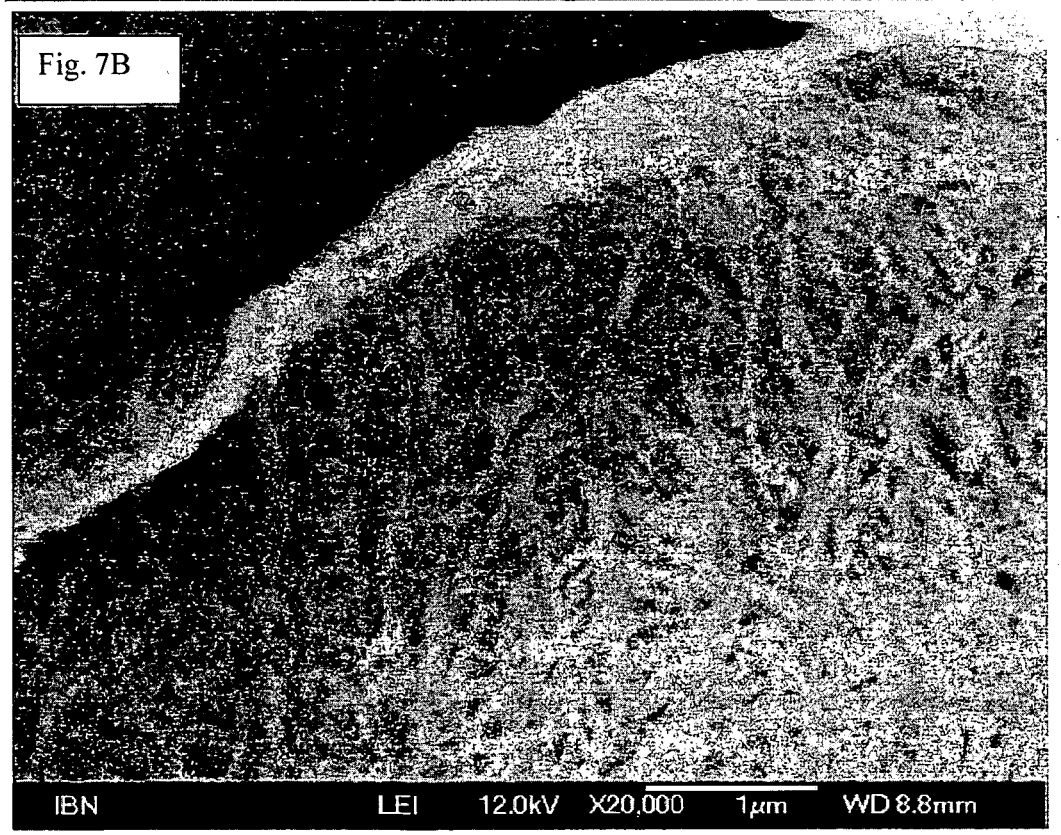
Figure 8A:
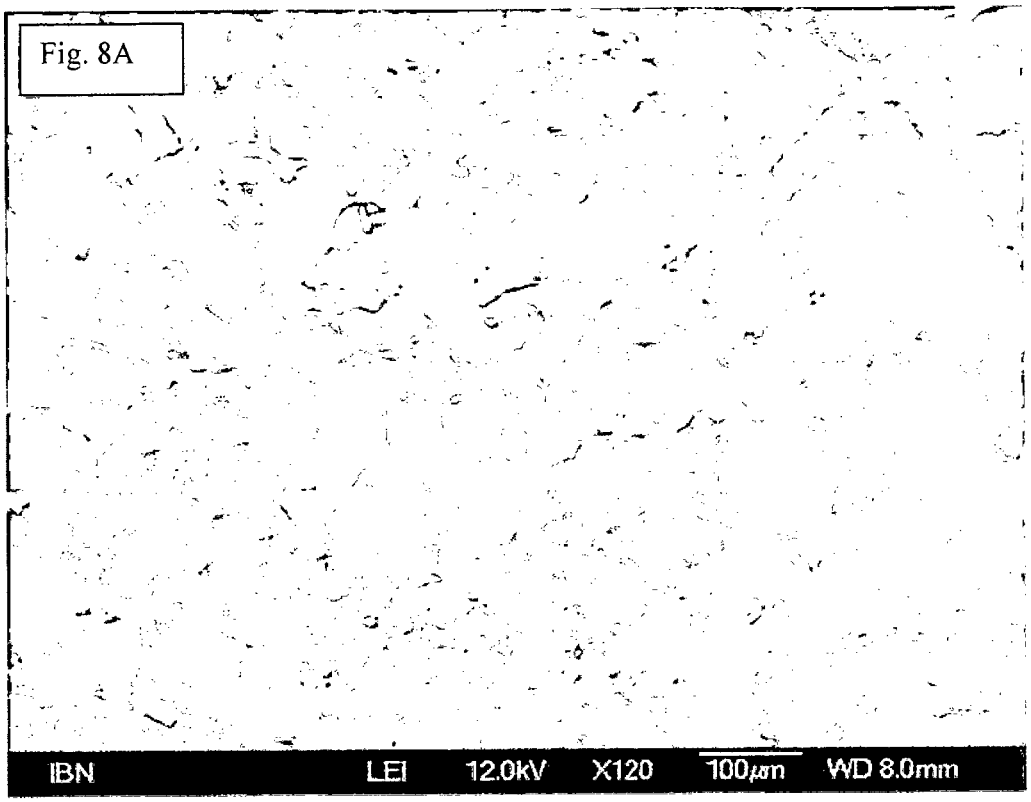
FIG. 8 shows field emission scanning electron microscopy (FESEM) images of hydrogels of Ac-AD 6 (D) (20 mg/ml) obtained at 120× (FIG. 8A), and 450× (FIG. 8B).
Figure 8B:
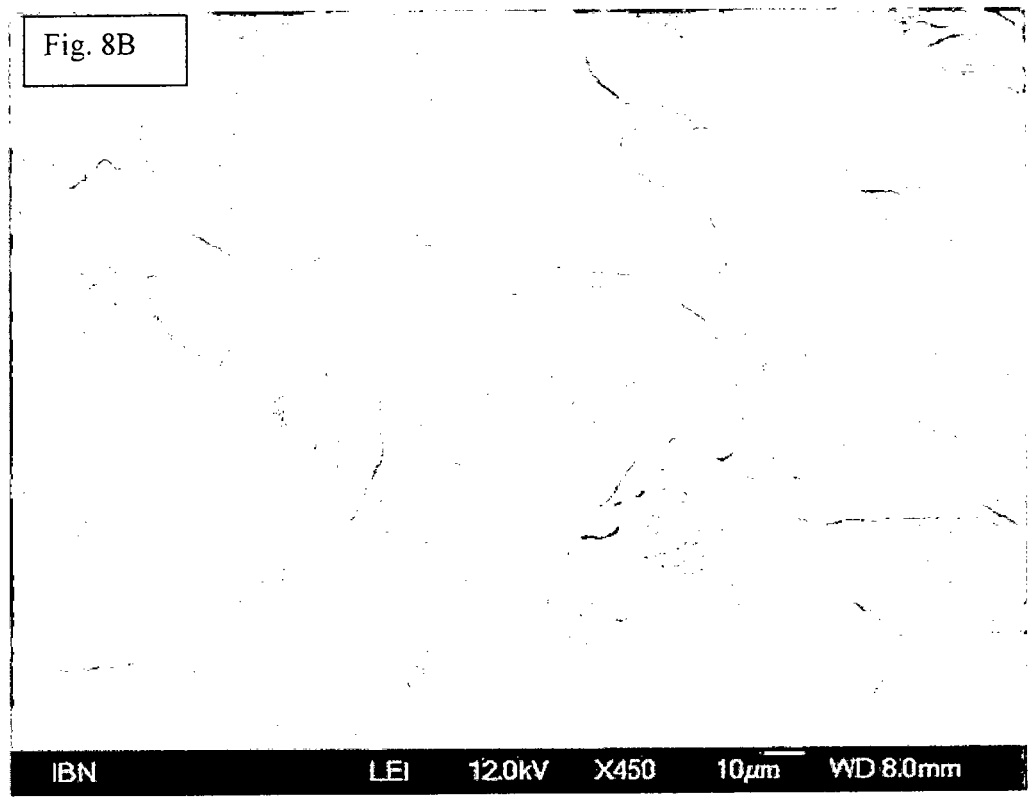
Figure 9A:
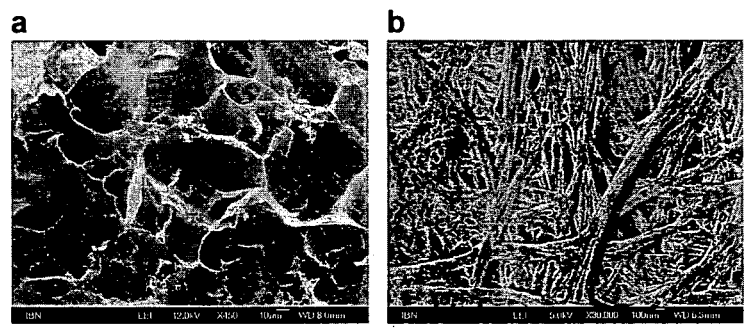
FIG. 9A a)-f) shows the morphology and structure evaluation of the peptide scaffolds as determined by field emission scanning electron microscopy (a-f) (a) A honeycomb porous structure is observed following lyophilization of 20 mg/mL Ac-AD$_6$ (D) hydrogel. The pores are bounded by membranes of condensed fibers as shown in close-up views of 15 mg/mL (b) and 20 mg/mL (c) Ac-ID$_3$ (L) hydrogels. Further magnification of 20 mg/mL Ac-AD$_6$ (L) hydrogel revealed single fibers (d, e). At lower concentrations, 0.1 mg/mL Ac-LD$_6$ (L), nanostructures are observed (f).
Figure 9A:
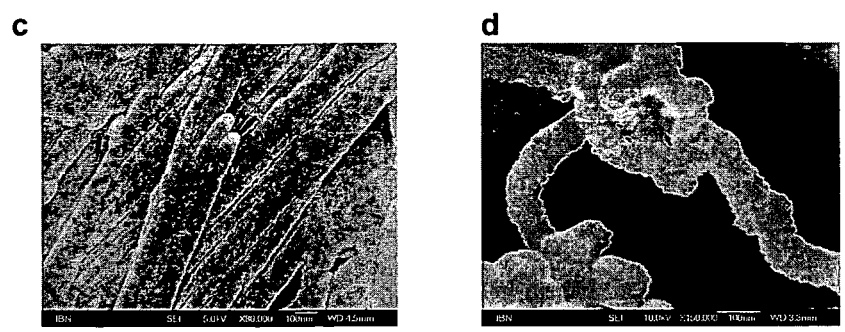
Figure 9A:
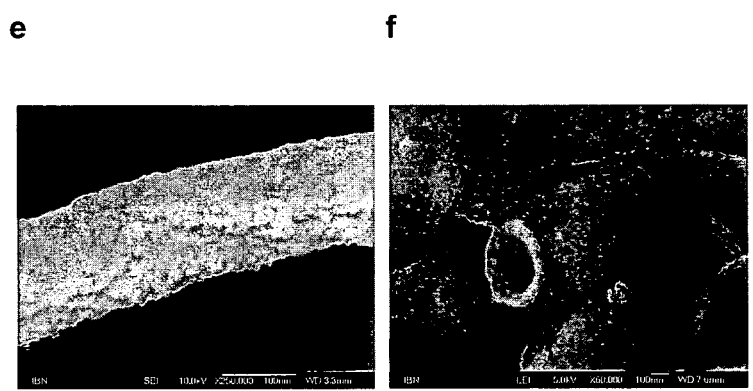
Figure 9B:
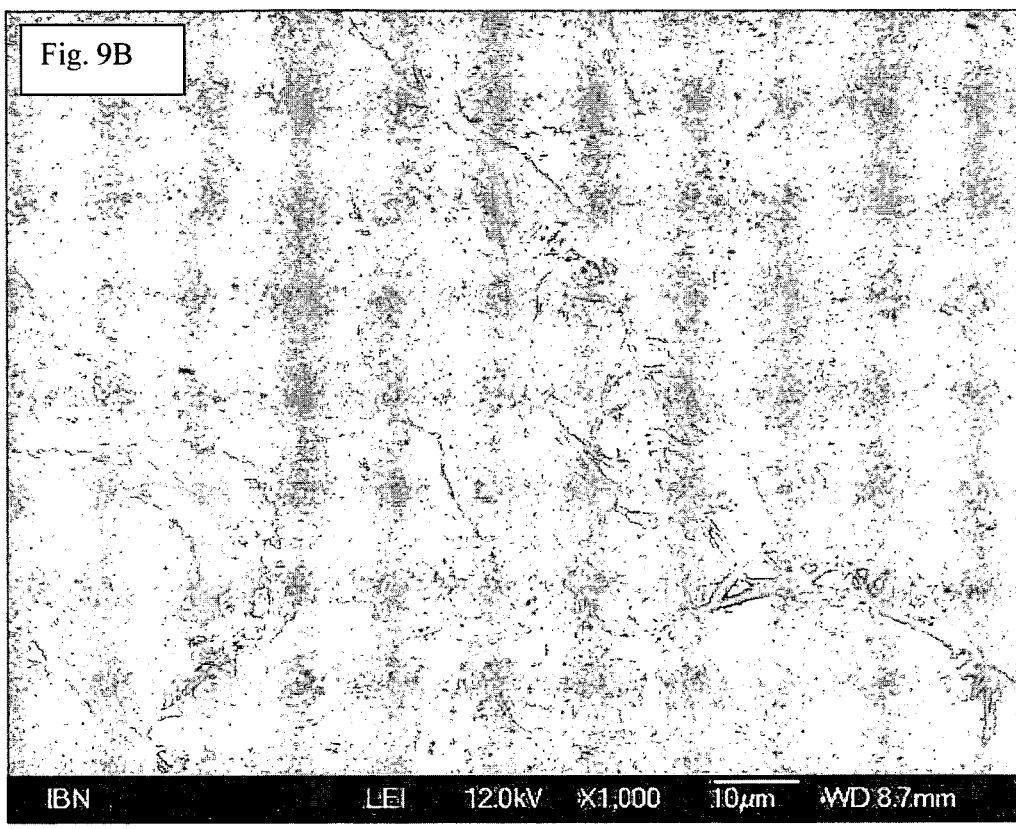
FIG. 9B shows an image obtained at a magnification of 1000×, HV of 12 KV, FIG. 9C obtained at a magnification of 2500×, HV of 12 KV, FIG. 9D obtained at a magnification of 4000×, FIV of 10 KV, FIG. 9E obtained at a magnification of 35000×, HV of 10 KV, FIG. 9F at a magnification of 80000×, HV of 5 KV, FIG. 9G obtained at a magnification of 120000×, HV of 10 KV, and FIG. 9H at a magnification of 200000×, HV of 10 KV.
Figure 9C:
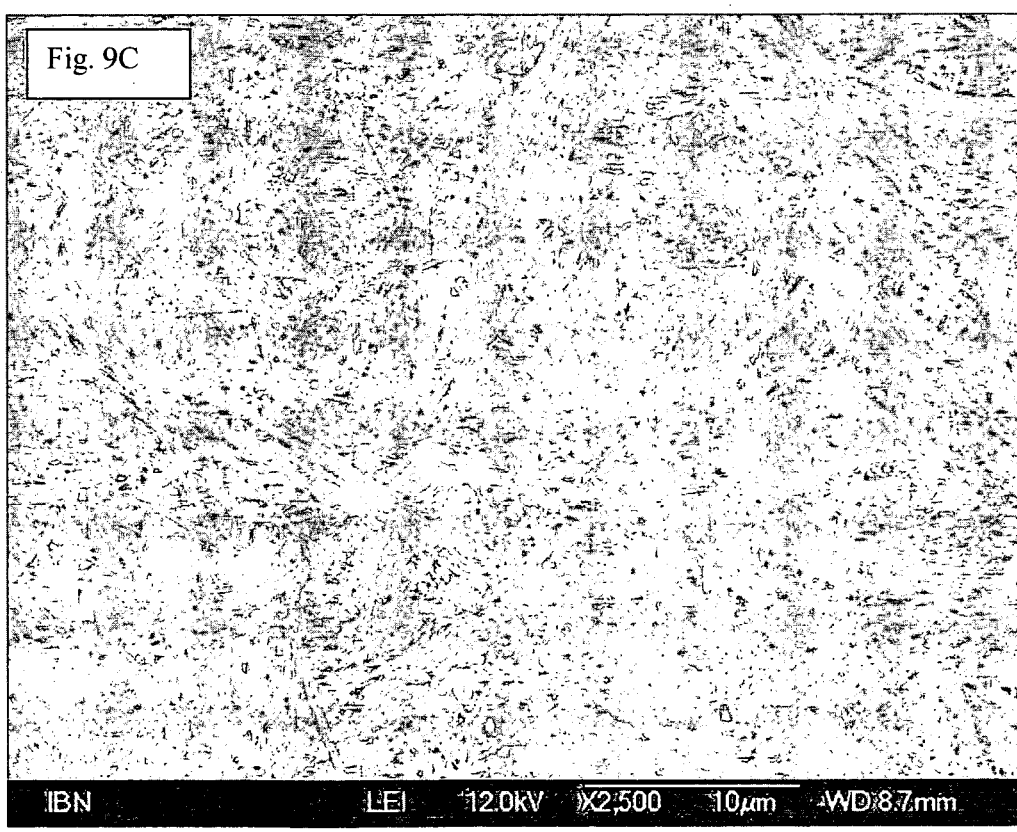
Figure 9D:
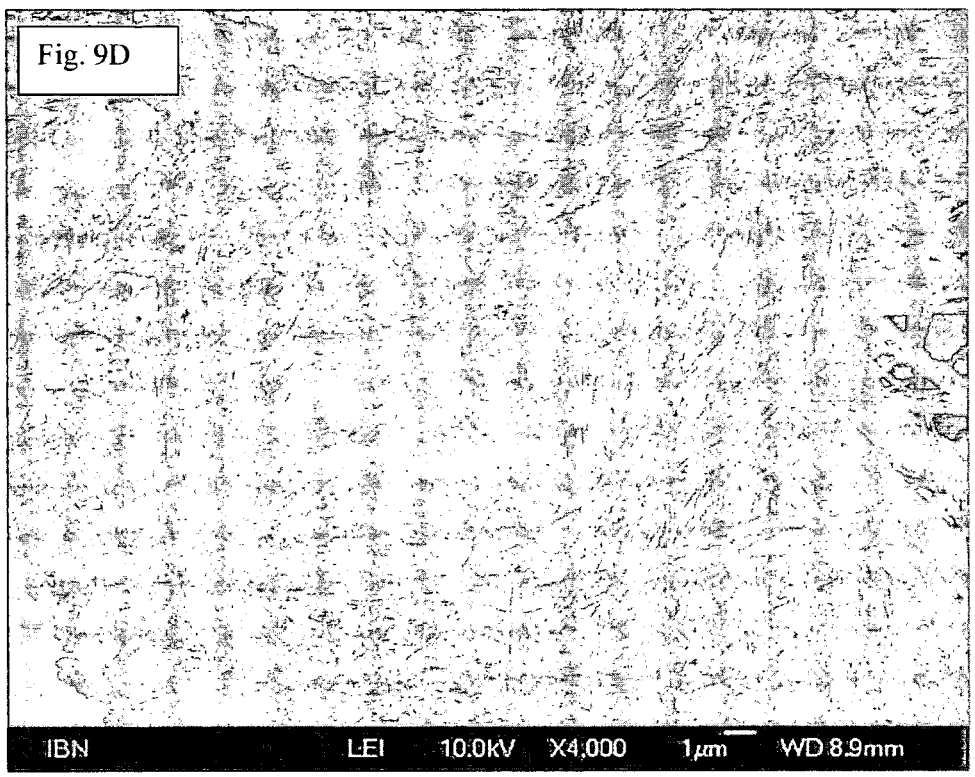
Figure 9E:
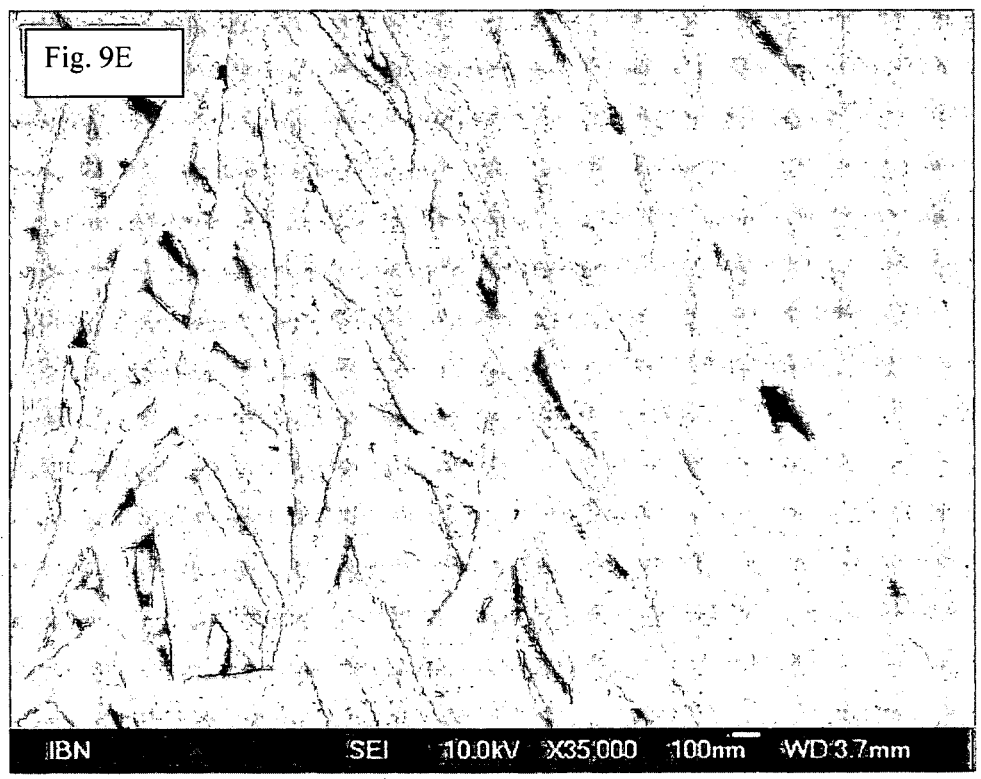
Figure 9G:
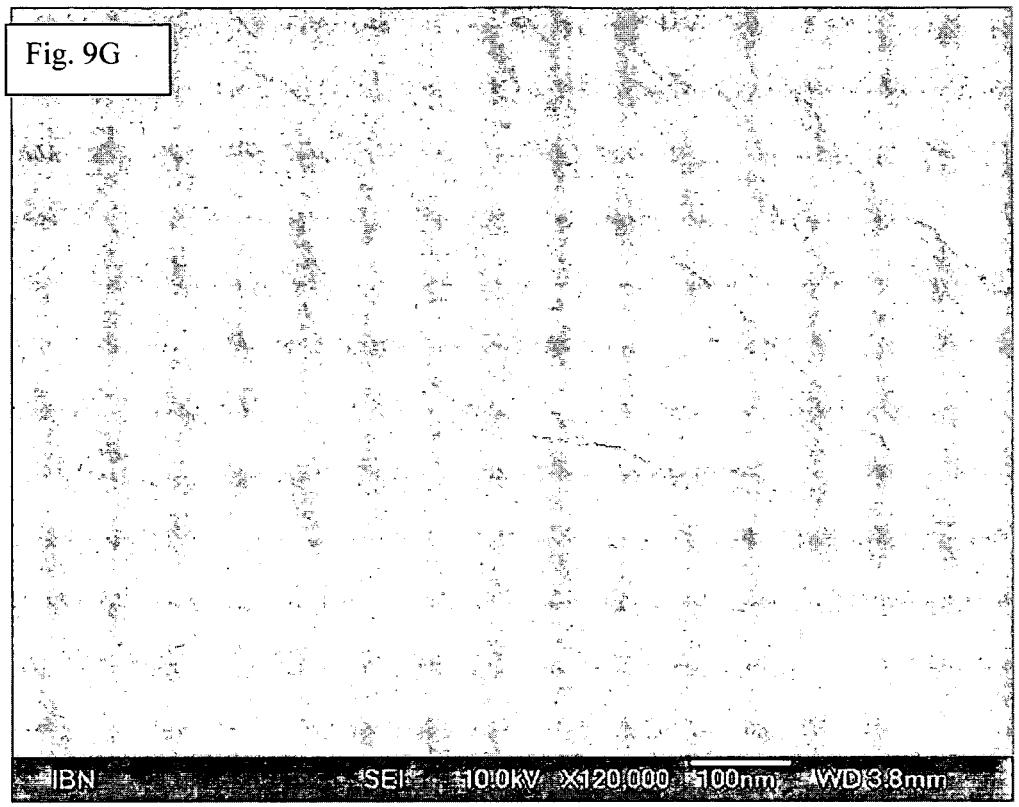
Figure 9H:
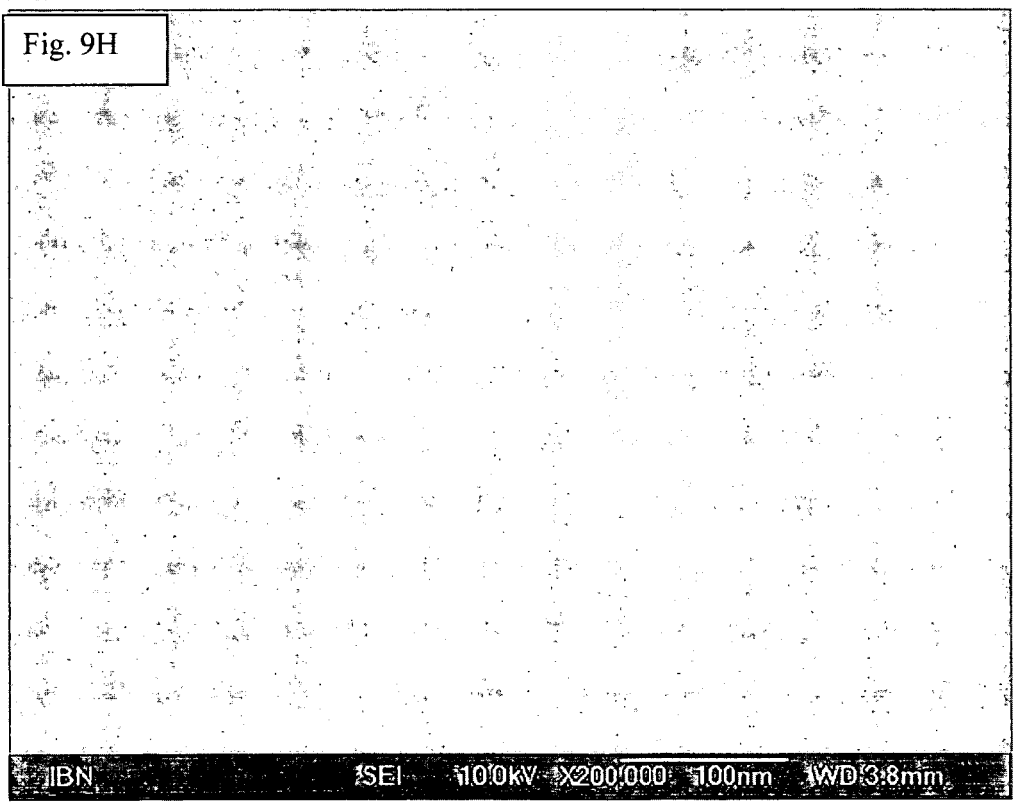
Figure 10:
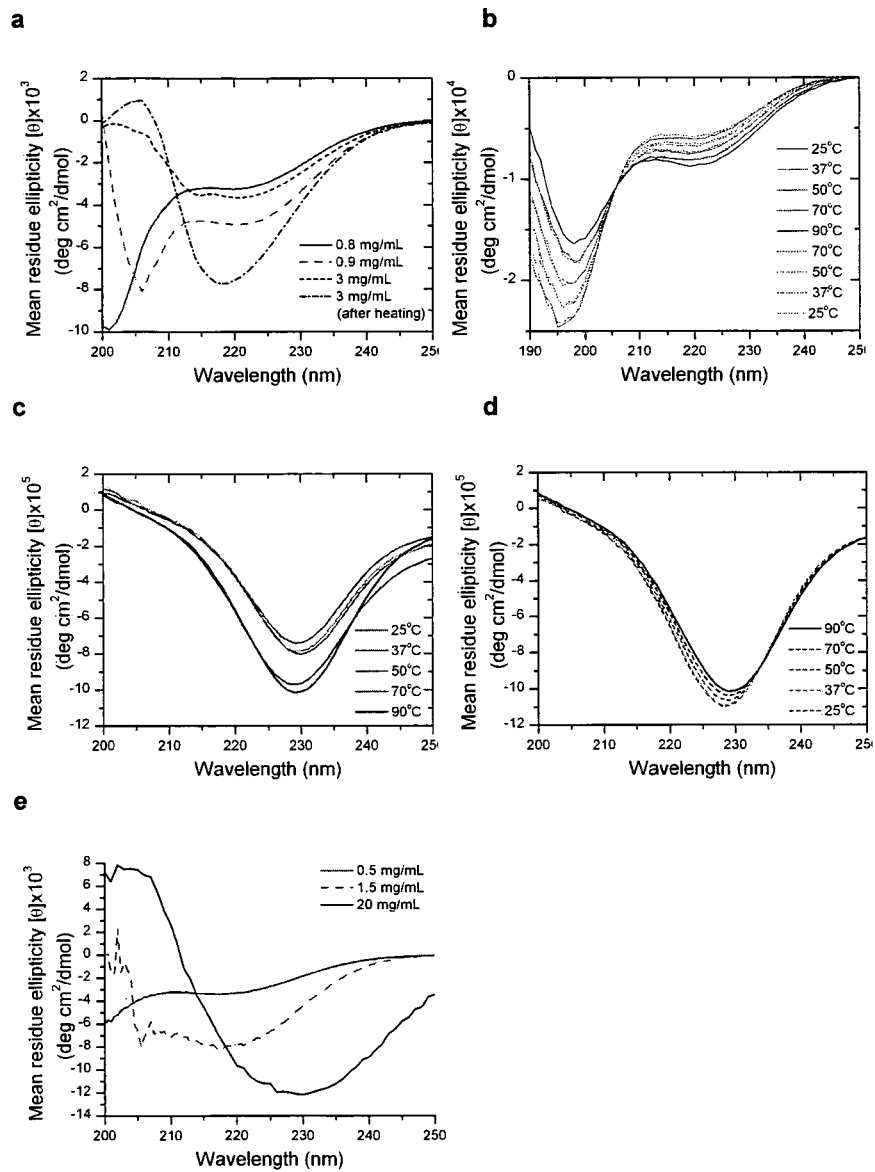
FIG. 10 shows (a) Far-UV CD spectra demonstrate that with increasing concentration there is the transition of Ac-LD$_6$ peptide conformation from random coil (below threshold concentration) to α-helical (222 and 208 nm peaks) and further β-type (negative band at 218 nm) structures. Heating the samples to facilitate gelation increased the β type aggregation. (b) Below threshold concentration, the random coil conformations of 0.2 mg/mL Ac-LD$_6$ were reversibly affected by step-wise temperature increases (solid lines) from 25° C. to 90° C. and cooling (dotted lines). (c, d) Above the threshold concentration in 1 mg/mL Ac-LD$_6$ gel, stepwise temperature increases (c) stabilized the β-type structures irreversibly, such that subsequent cooling (d) did not alter the CD spectra. (e) Far-UV CD spectra of AcID$_3$ at different concentrations. All curves were done at 25° C.
Figure 11:
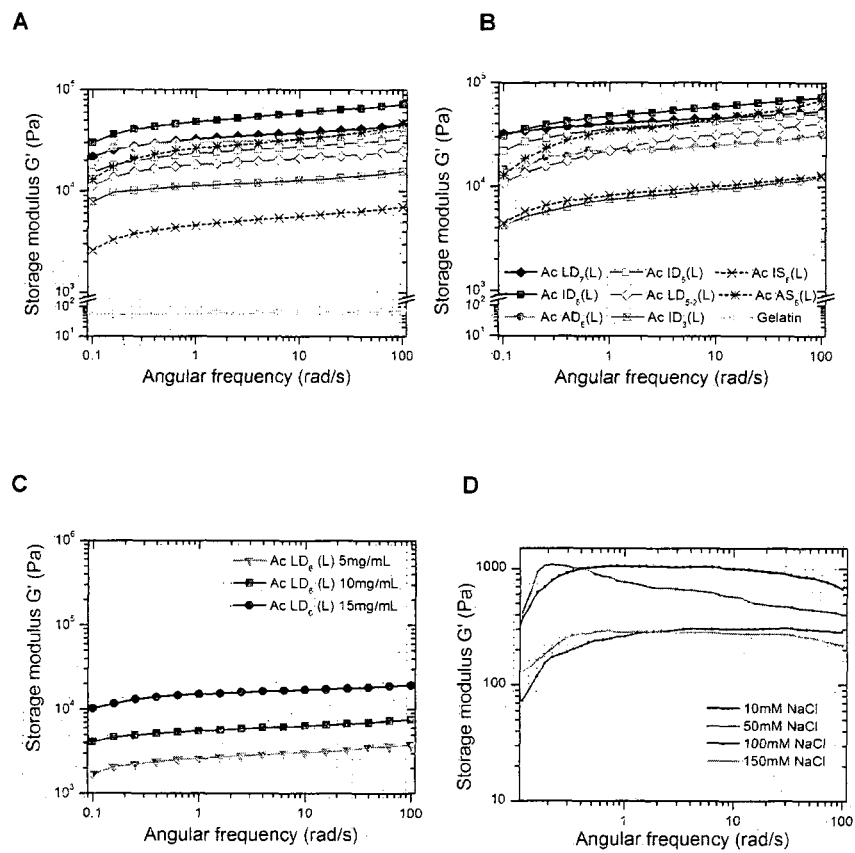
FIG. 11 shows Rheology.(a, b) The high mechanical strengths of different peptide hydrogels at 20 mg/mL concentration was determined by measuring storage moduli (G') as a function of angular frequency under 0.1% strain, at 25° C. and 50° C. respectively. The gels demonstrate good thermal stability compared to gelatin, which liquidified at 50° C. (hence excluded in 4B). (c) Mechanical strength is a function of concentration, as determined from oscillatory frequency sweep studies using Ac-LD$_6$ (L) under 0.1% strain at 25° C. (d) Increasing salt concentration (NaCl) decreases G', reducing the rigidity of 10 mg/mL Ac-LD$_6$ (L) hydrogels.
Figure 12:
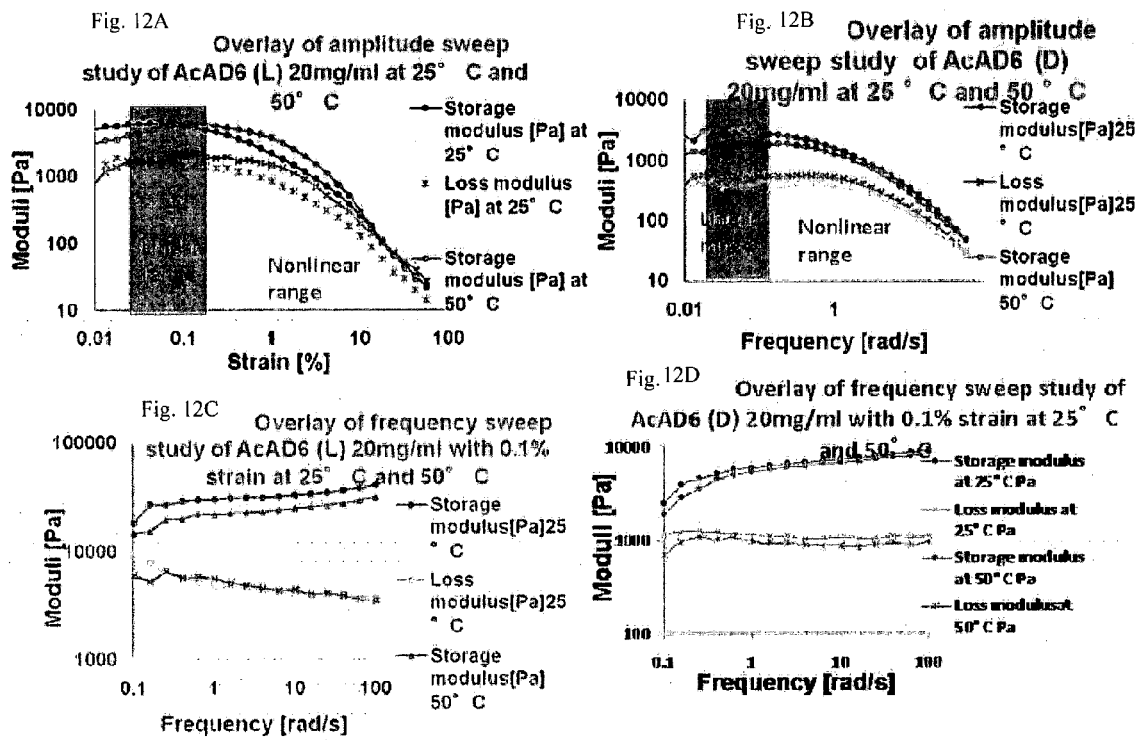
FIG. 12 shows a further example of a rheology measurement for peptide based hydrogels.
Figures 13, 14:
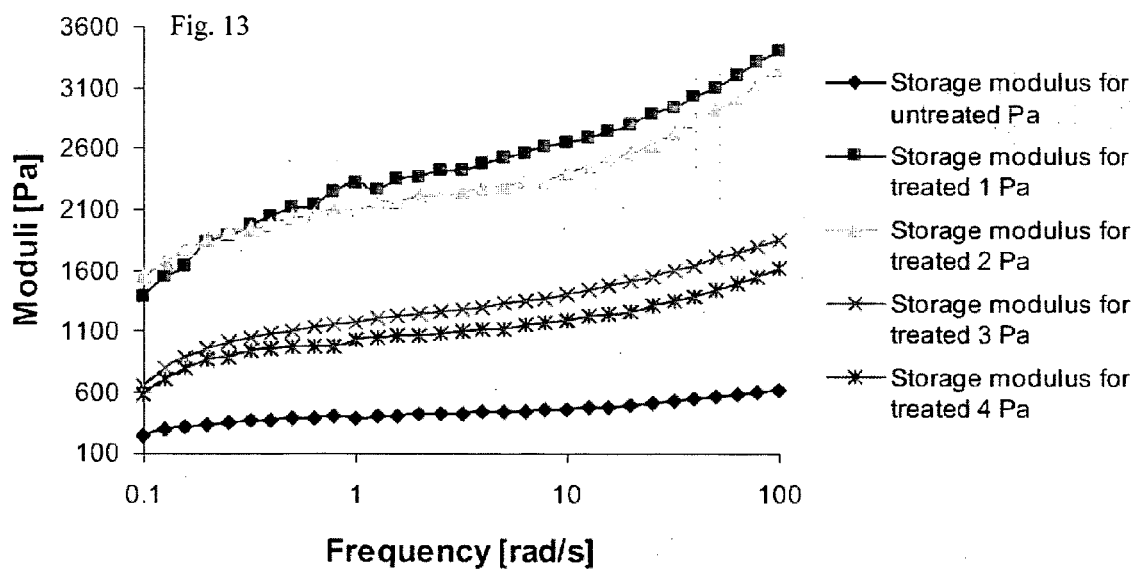
FIG. 13 shows a further example of a rheology measurement for peptide based hydrogels. Depicted is a frequency sweep study of a uv cross-linked peptide at a temperature of 25° C. with 0.1% strain.
FIG. 14 depicts rheology measurements for gelatin-1890 (type A, porcine skin). This figure shows moduli data obtained at 25° C. when applying different frequencies.
Figure 15A:
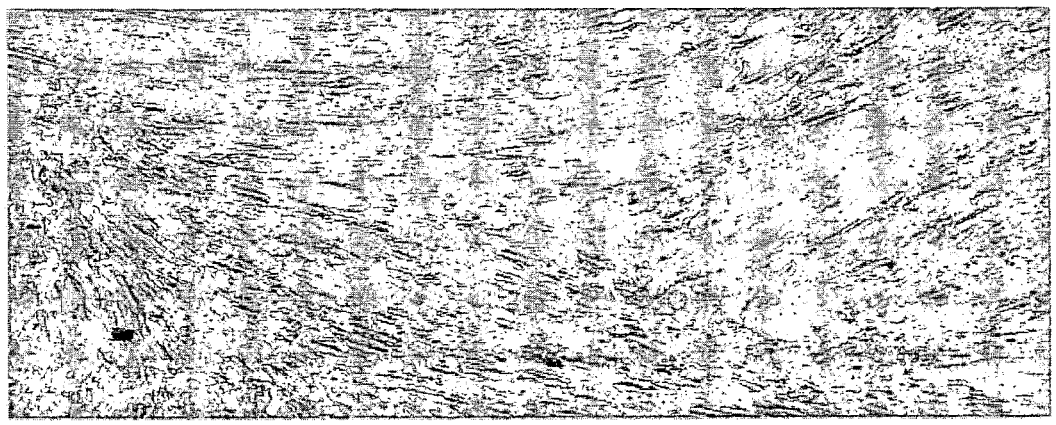
FIG. 15A shows a microscopy image of human primary renal tubule cells (HPRTC) after 72 hours after seeding on a hydrogel of Ac-LD$_6$ (L) in DMEM medium, grown at optimum conditions.
Figure 15B:
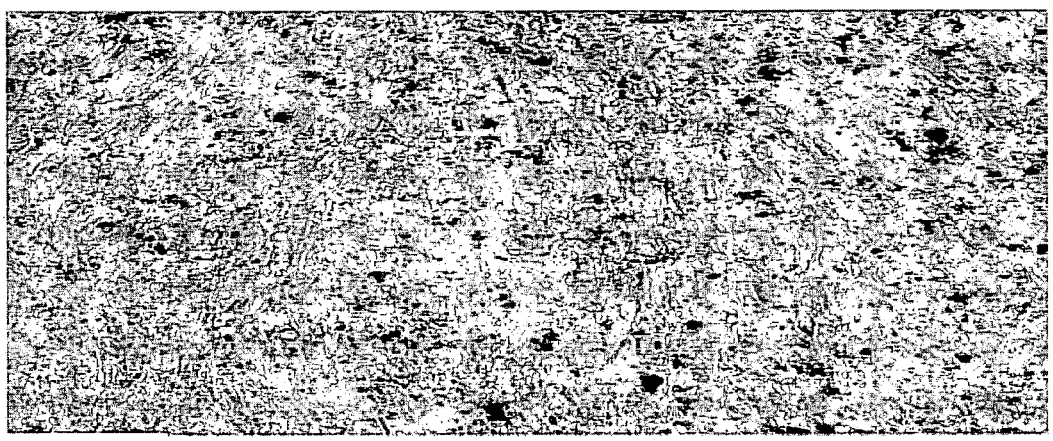
FIG. 15B shows microscopy images of human primary renal tubule cells (HPRTC) after 72 hrs after seeding on tissue culture plastic, grown at optimum conditions.
Figure 15C:
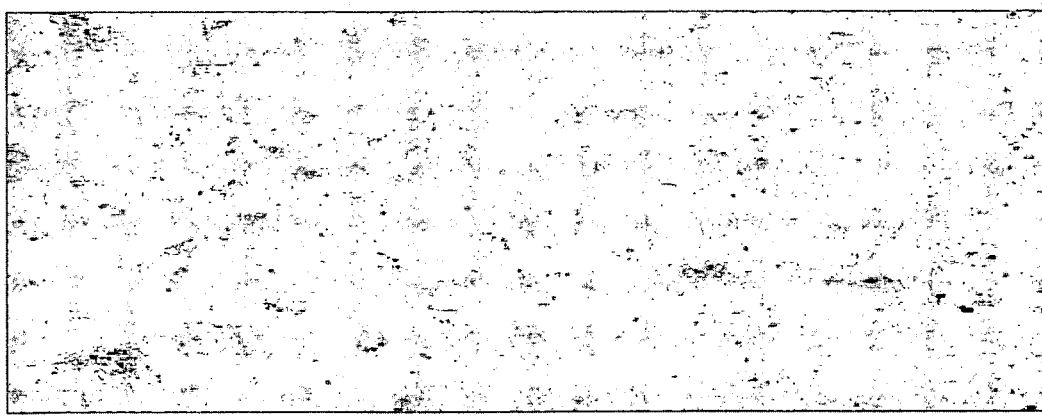
FIG. 15C shows microscopy images of human umbilical vein endothelial cells (HUVEC) after 72 hrs after seeding on gels of Ac-LD$_6$ (L) in DMEM medium, grown at optimum conditions.
Figure 15D:
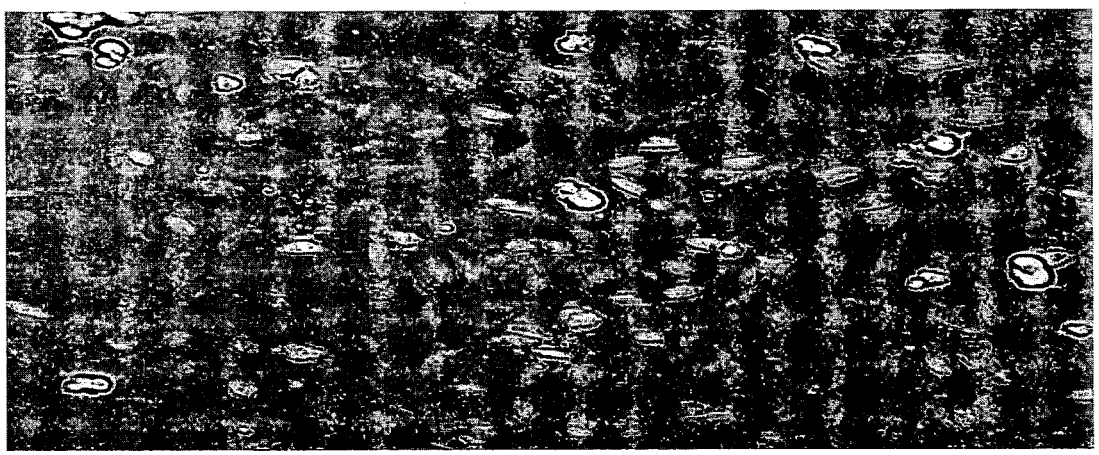
FIG. 15D shows microscopy images of human umbilical vein endothelial cells (HUVEC) after 72 hrs after seeding on tissue culture plastic, grown at optimum conditions.
Figure 16A:
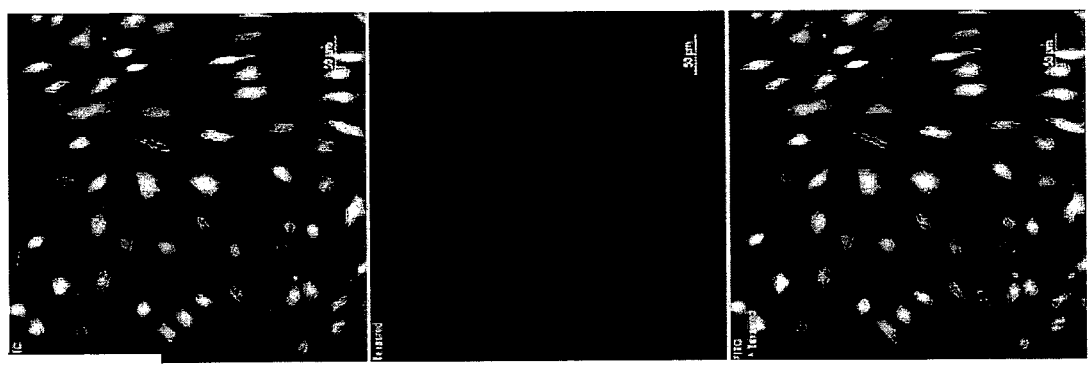
FIG. 16 is a further illustration on the viability of cells in presence of a hydrogel of the invention. Human fibroblast cells were cultured in the presence (FIG. 16A) and absence (FIG. 16B) of Ac-LD$_6$ (L) (5 mg/ml). Fluorescein isothiocyanate (FITC) stained cells (left panels), Texas red stained cells (center panels) and cells stained with both FITC and Texas red (right panels) are shown.
Figure 16B:
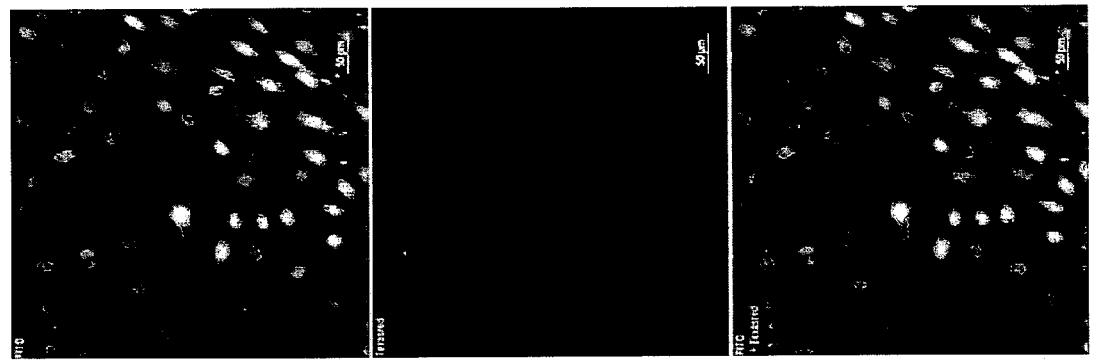

An exemplary embodiment of the invention provides a novel class of hydrogel-forming peptides/peptoids derived from inter alia natural amino acids. These peptides/peptoids are small amphiphilic peptides with a hydrophobic portion of aliphatic amino acids and one or two polar amino acids. The peptides/peptoids (typically 3-7-mers) are typically in the L- or D-form and can self assemble into supramolecular fibers which are organized into mesh-like structures. The hydrogels are generally characterized by a remarkable rigidity and are biocompatible and non-toxic. Depending on the peptide/peptoid sequence these hydrogels can show thermoresponsive or thixotropic character. By selecting the peptide assembling conditions the thickness and length of the fibers can be controlled. The rigid hydrogels can be used for cultivation of a variety of primary human cells, providing peptide scaffolds that can be useful in the repair and replacement of various tissues. Also disclosed is the procedure of preparing these hydrogels. Disclosed is further the use of respective hydrogels in applications such as cell culture, tissue engineering, plastic surgery, drug delivery, oral applications, cosmetics, packaging and the like as well as for technical applications, as for example for use in electronic devices which may include solar or fuel cells.

An exemplary of the present invention provides an amphiphilic peptide and/or peptoid capable of forming a hydrogel, i.e. a polymer network in which water is the dispersion medium. The amphiphilic peptide and/or peptoid includes one or more linear amphiphilic sequences, each having a polar and a non-polar portion. For sake of simplicity explanations are in the following to a large extent focused on amphiphilic peptides and/or peptoids that consist of a single respective linear sequence. In these explanations a respective peptide and/or peptoid is denominated a "linear peptide and/or peptoid". Respective explanations apply to any linear sequence, which may also be included in an amphiphilic peptide and/or peptoid with a plurality of these linear sequences. Each of these linear sequences is individually selected. In some embodiments an amphiphilic peptide and/or peptoid disclosed herein includes several linear amphiphilic sequences, each of them differing from any other of the linear amphiphilic sequences. In some embodiments an amphiphilic peptide and/or peptoid disclosed herein includes several identical linear amphiphilic sequences. In one embodiment an amphiphilic peptide and/or peptoid disclosed herein includes a plurality of linear amphiphilic sequences, each linear amphiphilic sequence being identical to each other linear amphiphilic sequence.

A peptide and/or peptoid according to an exemplary embodiment of the invention includes o amphiphilic linear sequences. The symbol o represents an integer selected in the range from 1 to about 25, such as from 1 to about 20, from 1 to about 18, from 1 to about 15, from 1 to about 12, from 1 to about 10, from 1 to about 8, from 1 to about 6, from 1 to about 5 from 1 to about 4 or from 1 to about 3. In some embodiments these amphiphilic linear sequences are linked in a consecutive manner, thereby defining a linear portion of the peptide and/or peptoid. In some embodiments the peptide and/or peptoid has a backbone with one or more branches. In such an embodiment these amphiphilic linear sequences may be included on different branches.

As mentioned above, each of the o amphiphilic linear sequences is independently selected. A respective amphiphilic linear sequence has a length of n aliphatic amino acids. The symbol n represents an integer selected in the range from 3 to about 18, such as from 3 to about 15, from 3 to about 14, from 3 to about 13, from 3 to about 12, from 3 to about 11, from 3 to about 10, from 3 to about 9, from 3 to about 8 or from 3 to about 7, such as 3, 4, 5, 6, 7, 8, 9 or 10 aliphatic amino acids.

In some embodiments an amphiphilic linear sequence of a peptide and/or peptoid described herein is chiral, rendering the entire amphiphilic peptide and/or peptoid chiral. A corresponding linear peptide and/or peptoid, i.e. an embodiment that consists of a single respective linear sequence, is accordingly a chiral peptide or peptoid. A respective amphiphilic linear sequence may include any linear non-aromatic amino acid. The term "amino acid" as used herein refers to an alpha-amino carboxylic acid, i.e. a carboxylic acid with an amino group in the α-position. The respective amino group may be an —NH$_2$ group or an —NHR$^1$ group. The moiety R$^1$ may be any aliphatic group, whether alkyl, alkenyl or alkynyl, with a main chain that includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl.

A peptoid is an oligo(N-alkyl) glycine that, similar to the side chain connected to the a carbon atom (see below) of a peptide, at the amide nitrogen carries a moiety that is in the present invention an aliphatic moiety. Accordingly, in embodiments where an —NHR$^1$ group (supra) is included in the amino acid and the a carbon atom is included in a —CH$_2$— group, the reaction product of coupling a plurality of such amino acids may be called a peptoid. A peptoid can also be taken to differ from a peptide in that it carries its side chain at the amide nitrogen rather than at the a carbon atom.

Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

The term "amino acid" includes compounds in which the carboxylic acid group is shielded by a protecting group in the form of an ester (including an ortho ester), a silyl ester, an amide, a hydrazide, an oxazole, an 1,3-oxazoline or a 5-oxo-1,3,-oxazolidine. The term "amino acid" also includes compounds in which an amino group of the form —$NH_2$ or —$NHR^1$ (supra) is shielded by a protecting group. Suitable amino protecting groups include, but are not limited to, a carbamate, an amide, a sulfonamide, an imine, an imide, histidine, a N-2,5,-dimethylpyrrole, an N-1,1,4,4-tetramethyldisilylazacyclopentane adduct, an N-1,1,3,3-tetramethyl-1,3-disilisoindoline, an N-diphenylsilyldiethylene, an 1,3,5-dioxazine, a N-[2-(trimethylsilyl)ethoxy]methylamine, a N-(5,5-dimethyl-3-oxo-1-cyclohexenyl)amine, a N-4,4,4-trifluoro-3-oxo-1-butenylamine, a N-9-borabicyclononane and a nitroamine. A protecting group may also be present that shields both the amino and the carboxylic group such as e.g. in the form of a 2,2-dimethyl-4-alkyl-2-sila-5-oxo-1,3-oxazolidine. The alpha carbon atom of the amino acid typically further carries a hydrogen atom. The so called "side chain" attached to the alpha carbon atom, which is in fact the continuing main chain of the carboxylic acid, is an aliphatic moiety that may be linear or branched. The term "side chain" refers to the presence of the amino acid in a peptide (supra), where a backbone is formed by coupling a plurality of amino acids. An aliphatic moiety bonded to the a carbon atom of an amino acid included in such a peptide then defines a side chain relative to the backbone. As explained above, the same applies to an aliphatic moiety bonded to the amino group of the amino acid, which likewise defines a side chain relative to the backbone of a peptoid.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

An aliphatic moiety may be substituted or unsubstituted with one or more functional groups. Substituents may be any functional group, as for example, but not limited to, amino, amido, azido, carbonyl, carboxyl, keto, cyano, isocyano, dithiane, halogen, hydroxyl, nitro, or ganometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

As should be apparent from the above, the side chain of an amino acid in a peptide/peptoid described herein may be of a length of 0 to about 5, to about 10, to about 15 or to about 20 carbon atoms. It may be branched and include unsaturated carbon-carbon bonds. In some embodiments one or more natural amino acids are included in the peptide or peptoid. Such a natural amino acid may be one of the 20 building blocks of naturally occurring proteins.

In a peptide or peptoid, including a peptide/peptoid disclosed herein individual amino acids are covalently coupled via amide bonds between a carboxylic group of a first and an amino group of a second amino acid. A peptide and/or peptoid disclosed herein is non-repetitive, such that two amino acids coupled to each other are always different from one another.

The term amphiphilic refers to a compound that is soluble in both polar and non-polar fluids. It also encompasses multiphase compounds. The amphiphilic properties of the peptide and/or peptoid are due to the presence of both polar and non-polar moieties within the same peptide and/or peptoid. In this regard the peptide and/or peptoid may be of surfactant nature. Accordingly, the polar properties of a peptide and/or peptoid according to an embodiment of the invention are based on a polar moiety. Two such moiety are a —COOH side group, in particular in the form of a charged $COO^-$ group and an amino group. A further such moiety is a C-terminal —COOH group if it is present in free, unprotecetd form. Generally, a surfactant molecule includes a polar, typically hydrophilic, head group attached to a non-polar, typically hydrocarbon, moiety. Non-polar moieties of a peptide or peptoid include a hydrocarbon chain that does not carry a functional group.

An amphiphilic linear sequence included in a peptide and/or peptoid of an embodiment of the invention thus includes a polar moiety and a non-polar moiety. The polar moiety includes an aliphatic amino acid that carries a polar group such as a hydroxyl group, a thiol group, a seleno group, an amino group, an amide group, an ether group, a thioether group or a seleno ether group. Accordingly, the polar moiety may include an amino acid that carries a functional polar group with a proton such as hydroxyl, thiol, selenol, amine or amide. The polar moiety may also include the C-terminus or the N-terminus of the peptide and/or peptoid. The Q-terminus or the N-terminus may in such a case be present in the form of the free carboxyl or amino group, respectively, i.e. free of a protecting group.

Generally the polar moiety of a linear amphiphilic sequence of an amphiphilic peptide and/or peptoid of an embodiment of the invention is defined by a single amino acid, by two consecutive amino acids or by three consecutive amino acids that is/are coupled to the non-polar moiety of the peptide/peptoid. Accordingly, in some embodiments the polar moiety of the peptide/peptoid consists of two amino acids that are covalently coupled via an amide bond, both amino acids carrying a polar peptide/peptoid side chain. One of these two amino acids may be a terminal amino aid of the peptide/peptoid, defining its N- or C-terminus. In some embodiments the amphiphilic peptide/peptoid has a single amino acid with a polar side chain with the residual portion of the peptide/peptoid defining the non-polar moiety. In some embodiments the amphiphilic peptide/peptoid has two amino acids with a polar side chain while the residual portion of the peptide/peptoid defines the non-polar moiety. As three illustrative examples of a respective polar side chain may serve 4-methyl-4-thio-pentyl, 6-ethoxycarbonyl-4,5-dimethylhexyl and 6-hydroxy-4-(1-hydroxyethyl)-hexyl groups. As used herein, the numbering of corresponding peptide/peptoid side chains is started with "1" at the carbon atom that is covalently bonded to the α-carbon atom of the amino acid or to the amino group of the amino acid, respectively. Amino acids included in the polar moiety may be or include, but are not limited to, aspartic acid, asparagine, glutamic acid, 4-fluoro-glutamic acid, 2-aminoadipic acid, γ-carboxy-glutamic acid, 4-tert-butyl aspartic acid, glutamine, 5-N-ethyl-glutamine (theanine), citrulline, thio-citrulline, cysteine, homocysteine, methionine, ethionine, selenomethionine, telluromethionine, threonine, allo-threonine, serine, homoserine, arginine, homoarginine, ornithine, lysine, 5-hydroxy-lysine and N(6)-carboxymethyllysine. Any such amino acid may be present in the L- or D-form.

The amphiphilic linear sequence of the amphiphilic peptide/peptoid of an embodiment of the invention can be defined as having n amino acids. Where a single amino acid with a polar side chain is included in the amphiphilic linear sequence, the non-polar moiety may then be taken to have n-1 amino acids. In this case the polar moiety consists of exactly one amino acid, such amino acid being selected from any amino acids of the foregoing paragraph. Where two consecutive amino acids with a polar side chain are included in the amphiphilic linear sequence of the peptide/peptoid, the non-polar moiety may then be taken to have n-2 amino acids. In this case the polar moiety consists of exactly two amino acids. Where three consecutive amino acids with a polar side chain are included in the amphiphilic linear sequence, the non-polar moiety may then be taken to have n-3 amino acids. In this case the polar moiety consists of exactly three amino acids. In embodiments where the polar moiety consists of two amino acids, the polar moiety may have a sequence selected from Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gln, Asp-Asn, Asn-Asp, Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu. In embodiments where the polar moiety consists of three amino acids, the polar moiety may have a sequence selected from Asn-Asn-Asn, Asn-Asn-Asp, Asn-Asp-Asn, Asp-Asn-Asn, Asp-Asp-Asn, Asp-Asn-Asp, Asp-Asp-Asp, Asn-Asn-Gln, Asn-Asn-Gln, Asn-Gln-Asn, Gln-Asn-Asn, Glu-Glu-Glu, Gln-Gln-Gln, Asn-Gln-Gln, Asn-Glu-Gln, Asp-Asn-Glu, Gln-Asn-Asn, Gln-Asn-Asn, Glu-Asp-Gln, Asp-Gln-Asp, Asn-Glu-Asp, Glu-Asn-Gln, Asp-Glu-Gln, Asn-Glu-Gln, Glu-Asp-Asn, and Gln-Asp-Asn, Thr-Thr-Thr, Ser-Ser-Ser, Asn-Thr-Thr, Asn-Ser-Ser Asn-Ser-Thr, Asn-Thr-Ser Asp-Asn-Ser, Ser-Asn-Asn, Thr-Asn-Asn, Ser-Asp-Thr, to name a few.

The amphiphilic linear sequence of the peptide/peptoid has a net charge at physiological pH. The term "physiological pH" is known to those in the art to refer to the pH value of blood, which has typically a pH value of about 7.4. In embodiments where the amphiphilic linear sequence is arranged at the C- or N-terminus of the peptide/peptoid, the respective terminus may provide the corresponding net charge. In embodiments where the amphiphilic linear sequence is not arranged at the C- or N-terminus of the peptide/peptoid, the polar moiety of the amphiphilic linear sequence includes one or more amino acids that have a side chain with a functional group that is charged at physiological pH. Illustrative examples of a respective functional group include an amino, a nitro-, a guanidino, a esteryl, a sulfonyl or a carboxyl group. In some embodiments the net charge of the amphiphilic linear sequence is, as a positive or as a negative charge, equal to or smaller than the number of amino acids included in the polar moiety thereof. In some embodiments the net charge of the amphiphilic linear sequence is one of −3, −2 or −1. In some embodiments the net charge of the amphiphilic linear sequence is +1, +2 or +3.

The respective polar side chain of an amino acid of the polar moiety, coupled to the α-carbon atom of the amino acid (supra) and/or to the amino group thereof, may typically be defined by a main chain that includes 1 to about 20, including 1 to about 15, 1 to about 10 or 1 to about 5 carbon atoms. For sake of clarity it is recited that the term "side chain" is used relative to the backbone of the peptide and/or peptoid. This peptide and/or peptoid side chain may be branched and thus be defined by a main chain and branches. Both the main chain and branches, if present, of the peptide and/or peptoid side chain may include one or more double or triple bonds (supra). Examples of side chains include, but are not limited to, methyl, ethyl, propyl, isopropyl, propenyl, propinyl, butyl, butenyl, sec-butyl, tert-butyl, isobutyl, pentyl, neopentyl, isopentyl, pentenyl, hexyl, 3,3 dimethylbutyl, heptyl, octyl, nonyl or decyl groups. The functional polar group is bonded to this the peptide and/or peptoid side chain.

In some embodiments the polar moiety of the amphiphilic linear sequence includes two identical amino acids. Where these amino acids are naturally occurring amino acids, they may for example define one of the sequences Lys-Lys, Gln-Gln, Glu-Glu, Asp-Asp, Asn-Asn, Met-Met, Thr-Thr, Arg-Arg or Ser-Ser. The term "naturally occurring" in this context refers to the 20 amino acids into which the genetic code is directly being translated by any organism. Such two identical polar amino acids may for example be adjacent to the non-polar moiety.

In some embodiments the amphiphilic linear sequence of the peptide/peptoid has a hydrophobic tail of aliphatic amino acids and at least one polar, including a charged, amino acid head group.

The non-polar moiety includes an amino acid, generally at least two amino acids, with a hydrocarbon chain that does not carry a functional group. The respective side chain, coupled to the a-carbon atom of the amino acid (supra), may have a main chain that includes 0 to about 20 or 1 to about 20, including 0 to about 15, 1 to about 15, 0 to about 10, 1 to about 10, 1 to about 5 or 0 to about 5 carbon atoms. The non-polar moiety may thus include an amino acid without side chain, i.e. glycine. The peptide and/or peptoid side chain may be branched (supra) and include one or more double or triple bonds (supra). Examples of peptide and/or peptoid side chains include, but are not limited to, methyl, ethyl, propyl, isopropyl, propenyl, propinyl, butyl, butenyl, sec-butyl, tert-butyl, isobutyl, pentyl, neopentyl, isopentyl, pentenyl, hexyl, 3,3 dimethylbutyl, heptyl, octyl, nonyl or decyl groups. As a few illustrative examples, the non-polar moiety may include an amino acid of alanine, valine, leucine, isoleucine, norleucine, norvaline, 2-(methylamino)-isobutyric acid, 2-amino-5-hexynoic acid. Such an amino acid may be present in any desired configuration. Bonded to the non-polar moiety may also be the C-terminus or the N-terminus of the peptide/peptoid. Typically the C-terminus or the N-terminus is in such a case shielded by a protecting group (supra).

In some embodiments the non-polar moiety includes a sequence of amino acids that is arranged in decreasing or increasing size. Hence, a portion of the amino acids of the non-polar moiety may be arranged in a general sequence of decreasing or increasing size. Relative to the direction from N- to C-terminus or from C- to N-terminus this general sequence can thus be taken to be of decreasing size. By the term "general sequence" of decreasing or increasing size is meant that embodiments are included in which adjacent amino acids are of about the same size as long as there is a general decrease or increase in size. Within a general sequence of decreasing size the size of adjacent amino acids of the non-polar moiety is accordingly identical or smaller in the direction of the general sequence of decreasing size. In some embodiments the general sequence of decreasing or increasing size is a non-repetitive sequence.

As an illustrative example, where a respective portion of amino acids is a sequence of five amino acids, the first amino acid may have a 3,4-dimethyl-hexyl side chain. The second amino acid may have a neopentyl side chain. The third amino acid may have a pentyl side chain. The fourth amino acid may have a butyl side chain. The fifth amino acid may be glycine, i.e. have no side chain. Although a neopentyl and a pentyl side chain are of the same size, the general sequence of such a non-polar peptide portion is decreasing in size. As a further illustrative example of a general sequence of decreasing size in a non-polar moiety the respective non-polar portion may be a sequence of three amino acids. The first amino acid may have an n-nonyl side chain. The second amino acid may have a 3-ethyl-2-methyl-pentyl side chain. The third amino acid may have a tert-butyl side chain. As yet a further illustrative example of a general sequence of decreasing size in a non-polar moiety, the non-polar moiety may be a sequence of nine amino acids. The first amino acid may have a 4-propyl-nonyl side chain. The second amino acid may have an n-dodecyl side chain. The third amino acid may have a 6,6-diethyl-3-octenyl side chain. An n-dodecyl side chain and a 6,6-diethyl-3-octenyl side chain both have 12 carbon atoms and thus again have a comparable size, Nevertheless, the 6,6-diethyl-3-octenyl group includes an unsaturated carbon-carbon bond and is thus of slightly smaller size than the dodecyl group. The fourth amino acid may have a 2-methylnonyl side chain. The fifth amino acid may have a 3-propyl-hexyl side chain. The sixth amino acid may have an n-hexyl side chain. The seventh amino acid may have a 2-butynyl side chain. The 8th amino acid may have an isopropyl side chain. The ninth amino acid may have a methyl side chain.

Where a portion of the amino acids of the non-polar moiety arranged in a general sequence of decreasing (or increasing) size only contains naturally occurring amino acids (whether in the D- or the L-form), it may for example have a length of five amino acids, such as the sequence leucine-isoleucine-valine-alanine-glycine or isoleucine-leucine-valine-alanine-glycine. A general sequence of decreasing size of only natural amino acids may also have a length of four amino acids. Illustrative examples include the sequences isoleucine-leucine-valine-alanine, leucine-isoleucine-valine-alanine, isoleucine-valine-alanine-glycine, leucine-valine-alanine-glycine, leucine-isoleucine-alanine-glycine, leucine-isoleucine-valine-glycine, isoleucine-leucine-alanine-glycine or isoleucine-leucine-valine-glycine. A general sequence of decreasing size of only natural amino acids may also have a length of three amino acids. Illustrative examples include the sequences isoleucine-valine-alanine, leucine-valine-alanine, isoleucine-valine-glycine, leucine-valine-glycine, leucine-alanine-glycine, isoleucine-alanine-glycine or isoleucine-leucine-alanine. A general sequence of decreasing size of only natural amino acids may also have a length of two amino acids. Illustrative examples include the sequences isoleucine-valine, leucine-valine, isoleucine-alanine, leucine-alanine, leucine-glycine, isoleucine-glycine, valine-alanine, valine-glycine or alanine-glycine.

In some embodiments the direction of decreasing size of the above defined general sequence of decreasing size is the direction toward the polar moiety of the amphiphilic linear sequence. Accordingly, in such embodiments the size of adjacent amino acids within this portion of the non-polar moiety is accordingly identical or smaller in the direction of the polar moiety. Hence, as a general trend in such an embodiment, the closer to the polar moiety of the amphiphilic linear sequence, the smaller is the overall size of a peptide and/or peptoid side chain throughout the respective general sequence of decreasing size. In the above illustrative example of a general sequence of three amino acids with a n-nonyl, a 3-ethyl-2-methyl-pentyl and a tert-butyl side chain, the next amino acid may be polar in that it carries a peptide/peptoid side chain with a polar functional group. As an illustrative example, adjacent to the tert-butyl side chain within the peptide/peptoid there may be a 3-carboxy-n-butyl side chain.

In some embodiments the entire non-polar moiety of the amphiphilic linear peptide and/or peptoid or the amphiphilic linear sequence, respectively, consists of the general sequence of decreasing (or increasing) size. In such an embodiment the general sequence of decreasing (or increasing) size may have a length of n-m amino acids (cf. above). In some embodiments the general sequence of decreasing or increasing size is flanked by further non-polar side chains of the peptide/peptoid. In one embodiment the general sequence of decreasing (or increasing) size has a length of n-m-1 amino acids. In this embodiment there is one further amino acid included in the peptide/peptoid, providing a non-polar peptide/peptoid side chain. This amino acid may be positioned between the general sequence of decreasing (or increasing) size and the polar amino acid, the polar amino acid may be positioned between this additional non-polar amino acid and the general sequence of decreasing (or increasing) size or the general sequence of decreasing (or increasing) size may be positioned between the polar amino acid and this additional non-polar amino acid. Typically the general sequence of decreasing (or increasing) size is positioned between the polar amino acid and this additional non-polar amino acid. The additional non-polar amino acid may for example define the N-terminus of the peptide/peptoid, which may be shielded by a protecting group such as an amide, e.g. a propionic acyl or an acetyl group. Together with the general sequence of decreasing (or increasing) size as defined above it may define the non-polar portion of the peptide/peptoid. The polar amino acid may define the C-terminus of the peptide/peptoid. In this example the general sequence of decreasing (or increasing) size is thus flanked by the polar amino acid on one side and by the additional non-polar amino acid on the other side. In one embodiment where embodiment the general sequence of decreasing (or increasing) size has a length of n-m-1 amino acids, the remaining non-polar amino acid of the non-polar moiety of n-m amino acids is one of alanine and glycine.

As explained above, the polar moiety of the amphiphilic linear sequence may in some embodiments be defined by two or three consecutive amino acids. The polar moiety includes m aliphatic amino acids. Each of the m aliphatic amino acids is independently selected and carries an independently selected polar group. The symbol m represents an integer selected from 1, 2 and 3. The at least essentially non-polar moiety (supra) accordingly has a number of n-m, i.e. n-1, n-2 or n-3-amino acids. In some embodiments n is equal to or larger than m+2. In such an embodiment m may thus represent a number of n-2 or smaller.

In an embodiment where the entire non-polar moiety of the amphiphilic linear peptide and/or peptoid consists of the general sequence of decreasing (or increasing) size (supra), this non-polar moiety may thus have a length of n-2 or n-3 amino acids. In an embodiment where the amphiphilic linear peptide and/or peptoid has a further non-polar side chain in addition to the non-polar moiety of decreasing (or increasing) size, this additional non-polar side chain may be included in an amino acid that is directly bonded to an amino acid of the general sequence of decreasing (or increasing) size. The non-polar moiety may thus be defined by the non-polar moiety of decreasing (or increasing) size and the respective further amino acid with a non-polar side chain. In one such an embodiment where m=1, the non-polar moiety may thus have a length of n-2 amino acids, of which the non-polar moiety of decreasing (or increasing) size has a length of n-3 amino acids. The general sequence of decreasing (or increasing) size may be positioned between the two polar amino acids and this additional non-polar amino acid, or the additional non-polar amino acid may be positioned between the general sequence of decreasing (or increasing) size and the two polar amino acids. Typically the general sequence of decreasing (or increasing) size is positioned between the two polar amino acids and this additional non-polar amino acid. As mentioned above, one of the two polar amino acids may define the C-terminus of the peptide/peptoid. In this example the general sequence of decreasing (or increasing) size may thus be flanked by the two consecutive polar amino acids on one side and by the additional non-polar amino acid on the other side. Again, in some embodiments where m=1 the two consecutive polar amino acids may also be positioned between the general sequence of decreasing (or increasing) size and the additional non-polar amino acid, in which case the non-polar moiety has a first portion with a length of n-3 amino acids and a further portion of one amino acid.

Electrostatic forces, hydrogen bonding and van der Waals forces between amphiphilic linear sequences as defined above, including amphiphilic linear peptides and/or peptoids, result in these amphiphilic linear sequences to be coupled to each other. Without being bound by theory, thereby a cross-linking effect occurs that allows the formation of a hydrogel. In this regard the inventors have observed the formation of fibers based on helical structures.

The fibers formed of amphiphilic linear sequences of amphiphilic peptides and/or peptoids of an embodiment of the invention typically show high mechanical strength, which renders them particularly useful in tissue regeneration applications, for instance the replacement of damaged tissue. Amphiphilic peptides and/or peptoids of an embodiment of the invention have been observed to generally assemle into a fiber structure that resembles collagen fibers. Collagen, a component of soft tissue in the animal and human body, is a fibrous protein that provides most of the tensile strength of tissue. The mechanical strength of fibers of amphiphilic peptides and/or peptoids of an embodiment of the invention has been found to typically be much higher than that of collagen (cf. e.g. Figures) of gelatine, the hydrolysed form of collagen. An amphiphilic peptide and/or peptoid of an embodiment of the invention may thus be Included in a hydrogel that is used as permanent or temporary prosthetic replacement for damaged or diseased tissue.

The amphiphilic linear sequence of the peptide/peptoid, which may represent the entire amphiphilic peptide/peptoid (supra) has been found to show remarkable stability at physiological conditions, even at elevated temperatures. It is in some embodiments stable in aqueous solution at physiological conditions at ambient temperature for a period of time in the range from 1 day to 1 month or more. It may in some embodiments be stable in aqueous solution at physiological conditions at 90° C. for at least 1 hour, at least 2 hours, at least 3 hours, at least 4 hours or at least 5 hours.

An amphiphilic linear sequence of an amphiphilic peptide and/or peptoid of an embodiment of the invention, including an amphiphilic linear peptide and/or peptoid, is capable of providing a self assembling α-helical fiber in aqueous solution under physiological conditions. The peptides/peptoids (typically 3-7-mers) in the L- or D-form can self assemble into supramolecular helical fibers which are organized into mesh-like structures mimicking biological substances such as collagen. It has previously been observed in X-ray crystallography that peptides of a length of 3 to 6 amino acids with repetitive alanine containing sequences and an acetylated C-terminus take a helical conformation (Hatakeyama, Y, et al, Angew. Chem. Int. Ed. (2009) 8695-8698). Using peptides with an amphiphilic sequence of an embodiment of the invention, AcLD6 (L), the formation of aggregates has for example been observed already at 0.1 mg/ml. As the concentration of peptide is increased to 1 mg/ml, the peptide monomers were found to align to form fibrous structures. With a formation of fibers occurring under physiological conditions at concentrations below 2 mM a peptide/peptoid of an embodiment of the invention is well suited as an injectable hydrogel material that can form a hydrogel under physiological conditions. An embodiment of the invention thus also relates to an amphiphilic linear peptide and/or peptoid as defined above for tissue engineering as well as to a tissue engineering method that involves applying, including injecting a respective amphiphilic linear peptide and/or peptoid.

A hydrogel according to an embodiment of the present invention is typically characterized by a remarkable rigidity and are generally biocompatible and non-toxic. Depending on the selected peptide/peptoid sequence these hydrogels can show thermoresponsive or thixotropic character. Reliant on the peptide/peptoid assembling conditions the fibers differ in thickness and length. Generally rigid hydrogels are obtained that are well suited for cultivation of a variety of primary human cells, providing peptide/peptoid scaffolds that can be useful in the repair and replacement of various tissues. Disclosed is also a process of preparing these hydrogels. The exemplary usage of these hydrogels in applications such as cell culture, tissue engineering, plastic surgery, drug delivery, oral applications, cosmetics, packaging and the like is described, as well as for technical applications, as for example for use in electronic devices which might include solar or fuel cells.

As an amphiphilic linear sequence of the peptide/peptoid, a hydrogel of an embodiment of the invention shows high stability at physiological conditions, even at elevated temperatures. In some embodiments such a hydrogel is stable in aqueous solution at ambient temperature for a period of at least 7 days, at least 14 days, at least a month or more, such as at least 1 to about 6 months.

In some embodiments a hydrogel disclosed herein is coupled to a molecule or a particle, including a quantum dot, with characteristic spectral or fluorometric properties, such as a marker, including a fluorescent dye. A respective molecule may for instance allow monitoring the fate, position and/or the integrity of the hydrogel.

In some embodiments a hydrogel disclosed herein is coupled to a molecule with binding affinity for a selected target molecule, such as a microorganism, a virus particle, a peptide, a peptoid, a protein, a nucleic acid, a peptide, an oligosaccharide, a polysaccharide, an inorganic molecule, a synthetic polymer, a small organic molecule or a drug.

The term "nucleic acid molecule" as used herein refers to any nucleic acid in any possible configuration, such as single stranded, double stranded or a combination thereof. Nucleic acids include for instance DNA molecules (e.g., cDNA or genomic DNA), RNA molecules (e.g., mRNA), analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. In the present method of an embodiment of the invention typically, but not necessarily, an RNA or a DNA molecule will be used. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label. In some embodiments the nucleic acid molecule may be isolated, enriched, or purified. The nucleic acid molecule may for instance be isolated from a natural source by cDNA cloning or by subtractive hybridization. The natural source may be mammalian, such as human, blood, semen, or tissue. The nucleic acid may also be synthesized, e.g. by the triester method or by using an automated DNA synthesizer.

Many nucleotide analogues are known and can be used in nucleic acids and oligonucleotides used in the methods of exemplary embodiments of the invention. A nucleotide analogue is a nucleotide containing a modification at for instance the base, sugar, or phosphate moieties. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

A peptide may be of synthetic origin or isolated from a natural source by methods wellknown in the art. The natural source may be mammalian, such as human, blood, semen, or tissue. A peptide, including a polypeptide may for instance be synthesized using an automated polypeptide synthesizer. Illustrative examples of polypeptides are an antibody, a fragment thereof and a proteinaceous binding molecule with antibody-like functions. Examples of (recombinant) antibody fragments are Fab fragments, Fv fragments, single-chain Fv fragments (scFv), diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). An example of a proteinaceous binding molecule with antibody-like functions is a mutein based on a polypeptide of the lipocalin family (WO 03/029462, Beste et al., Proc. Natl. Acad. Sci. U.S.A. (1999) 96, 1898-1903). Lipocalins, such as the bilin binding protein, the human neutrophil gelatinase-associated lipocalin, human Apolipoprotein D or glycodelin, posses natural ligandbinding sites that can be modified so that they bind to selected small protein regions known as haptens. Examples of other proteinaceous binding molecules are the so-called glubodies (see e.g. internation patent application WO 96/23879), proteins based on the ankyrin scaffold (Mosavi, L. K., et al., Protein Science (2004) 13, 6, 1435-1448) or crystalline scaffold (e.g. internation patent application WO 01/04144) the proteins described in Skerra, J. Mol. Recognit. (2000) 13, 167-187, AdNectins, tetranectins and avimers. Avimers contain so called Adomains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Where desired, a modifying agent may be used that further increases the affinity of the respective moiety for any or a certain form, class etc. of target matter.

An example of a nucleic acid molecule with antibody-like functions is an aptamer. An aptamer folds into a defined three-dimensional motif and shows high affinity for a given target structure. Using standard techniques of the art such as solid-phase synthesis an aptamer with affinity to a certain target can accordingly be formed and immobilized on a hollow particle of an embodiment of the invention.

As a further illustrative example, a linking moiety such as an affinity tag may be used to immobilise the respective molecule. Such a linking moiety may be a molecule, e.g. a hydrocarbon-based (including polymeric) molecule that includes nitrogen-, phosphorus-, sulphur-, carben-, halogen- or pseudohalogen groups, or a portion thereof. As an illustrative example, the peptide/peptoid included in the hydrogel may include functional groups, for instance on a side chain of the peptide/peptoid, that allow for the covalent attachment of a biomolecule, for example a molecule such as a protein, a nucleic acid molecule, a polysaccharide or any combination thereof. A respective functional group may be provided in shielded form, protected by a protecting group that can be released under desired conditions. Examples of a respective functional group include, but are not limited to, an amino group, an aldehyde group, a thiol group, a carboxy group, an ester, an anhydride, a sulphonate, a sulphonate ester, an imido ester, a silyl halide, an epoxide, an aziridine, a phosphoramidite and a diazoalkane.

Examples of an affinity tag include, but are not limited to, biotin, dinitrophenol or digoxigenin, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala, the "myc" epitope of the transcription factor c-myc of the sequence Glu-Gln-Lys-Leu-Ile-Ser-Glu-Glu-Asp-Leu, or an oligonucleotide tag. Such an oligonucleotide tag may for instance be used to hybridise to an immobilised oligonucleotide with a complementary sequence. A further example of a linking moiety is an antibody, a fragment thereof or a proteinaceous binding molecule with antibody-like functions (see also above).

A further example of linking moiety is a cucurbituril or a moiety capable of forming a complex with a cucurbituril. A cucurbituril is a macrocyclic compound that includes glycoluril units, typically self-assembled from an acid catalyzed condensation reaction of glycoluril and formaldehyde. A cucurbit[n]uril, (CB[n]), that includes n glycoluril units, typically has two portals with polar ureido carbonyl groups. Via these ureido carbonyl groups cucurbiturils can bind ions and molecules of interest. As an illustrative example cucurbit[7] uril (CB[7]) can form a strong complex with ferrocenemethylammonium or adamantylammonium ions. Either the cucurbit[7]uril or e.g. ferrocenemethylammonium may be attached to a biomolecule, while the remaining binding partner (e.g.

ferrocenemethylammonium or cucurbit[7]uril respectively) can be bound to a selected surface. Contacting the biomolecule with the surface will then lead to an immobilisation of the biomolecule. Functionalised CB[7] units bound to a gold surface via alkanethiolates have for instance been shown to cause an immobilisation of a protein carrying a ferrocenemethylammonium unit (Hwang, I., et al., J. Am. Chem. Soc. (2007) 129, 4170-4171).

Further examples of a linking moiety include, but are not limited to an oligosaccharide, an oligopeptide, biotin, dinitrophenol, digoxigenin and a metal chelator (cf. also below). As an illustrative example, a respective metal chelator, such as ethylenediamine, ethylenediaminetetraacetic acid (EDTA), ethylene glycol tetraacetic acid (EGTA), diethylenetriaminepentaacetic acid (DTPA), N,N-bis(carboxymethyl) glycine (also called nitrilotriacetic acid, NTA), 1,2-bis(o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. In some embodiments a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligohistidine tag and copper ($Cu^{2+}$), nickel ($Ni^{2+}$), cobalt ($Co^{2+}$), or zink ($Zn^{2+}$) ions, which are presented by means of the chelator nitrilotriacetic acid (NTA).

Avidin or streptavidin may for instance be employed to immobilise a biotinylated nucleic acid, or a biotin containing monolayer of gold may be employed (Shumaker-Parry, J. S., et al., Anal. Chem. (2004) 76, 918). As yet another illustrative example, the biomolecule may be locally deposited, e.g. by scanning electrochemical microscopy, for instance via pyrrole-oligonucleotide patterns (e.g. Fortin, E., et al., Electroanalysis (2005) 17, 495). In other embodiments, in particular where the biomolecule is a nucleic acid, the biomolecule may be directly synthesised on the surface of the immobilisation unit, for example using photoactivation and deactivation. As an illustrative example, the synthesis of nucleic acids or oligonucleotides on selected surface areas (so called "solid phase" synthesis) may be carried out us ing electrochemical reactions using electrodes. An electrochemical deblocking step as described by Egeland & Southern (Nucleic Acids Research (2005) 33, 14, e125) may for instance be employed for this purpose. A suitable electrochemical synthesis has also been disclosed in US patent application US 2006/0275927. In some embodiments light-directed synthesis of a biomolecule, in particular of a nucleic acid molecule, including UV-linking or light dependent 5'-deprotection, may be carried out.

The molecule that has a binding affinity for a selected target molecule may be immobilised on the nanocrystals by any means. As an illustrative example, an oligo- or polypeptide, including a respective moiety, may be covalently linked to the surface of nanocrystals via a thio-ether-bond, for example by using co functionalized thiols. Any suitable molecule that is capable of linking a nanocrystal of an embodiment of the invention to a molecule having a selected binding affinity may be used to immobilise the same on a nanocrystal. For instance a (bifunctional) linking agent such as ethyl-3-dimethylaminocarbodiimide, N-(3-aminopropyl) 3-mercapto-benzamide, 3-aminopropyl-trimethoxysilane, 3-mercaptopropyl-trimethoxysilane, 3-(trimethoxysilyl) propyl-maleimide, or 3-(trimethoxysilyl) propyl-hydrazide may be used. Prior to reaction with the linking agent, the surface of the nanocrystals can be modified, for example by treatment with glacial mercaptoacetic acid, in order to generate free mercaptoacetic groups which can then employed for covalently coupling with an analyte binding partner via linking agents.

Embodiments of the present invention also include a hydrogel, which can be taken to be a water-swollen water-insoluble polymeric material. The hydrogel includes, including contains and consists of, a peptide and/or peptoid as defined above. Since a hydrogel maintains a three-dimensional structure, a hydrogel of an embodiment of the invention may be used for a variety of applications. Since the hydrogel has a high water content and includes amino acids, it is typically of excellent biocompatibility.

A hydrogel according to an embodiment of the invention is typically formed by self-assembly. The inventors have observed that the peptides/peptoids assemble into fibers that form mesh-like structures. Without being bound by theory hydrophobic interaction between non-polar portions of peptides/peptoids of an embodiment of the invention are contemplated to assist such self-assembly process.

The method of forming the hydrogel includes dissolving the peptide/peptoid in aqueous solution. Agitation, including mixing such as stirring, and/or sonication may be employed to facilitate dissolving the peptide/peptoid. In some embodiments the aqueous solution with the peptide/peptoid therein is exposed to a temperature below ambient temperature, such as a temperature selected from about 2° C. to about 15° C. In some embodiments the aqueous solution with the peptide/peptoid therein is exposed to an elevated temperature, i.e. a temperature above ambient temperature. Typically the aqueous solution is allowed to attain the temperature to which it is exposed. The aqueous solution may for example be exposed to a temperature from about 25° C. to about 85° C. or higher, such as from about 25° C. to about 75° C., from about 25° C. to about 70° C., from about 30° C. to about 70° C., from about 35° C. to about 70° C., from about 25° C. to about 60° C., from about 30° C. to about 60° C., from about 25° C. to about 50° C., from about 30° C. to about 50° C. or from about 40° C. to about 65° C., such as e.g. a temperature of about 40° C., about 45° C., about 50° C., about 55° C., about 60° C. or about 65° C. The aqueous solution with the peptide/peptoid therein may be maintained at this temperature for a period of about 5 min to about 10 hours or more, such as about 10 min to about 6 hours, about 10 min to about 4 hours, about 10 min to about 2.5 hours, about 5 min to about 2.5 hours, about 10 min to about 1.5 hours or about 10 min to about 1 hour, such as about 15 min, about 20 min, about 25 min, about 30 min, about 35 min or about 40 min.

A hydrogel according to an embodiment of the invention may be included in a fuel cell, where it may for example provide a substrate between the anode and the cathode. a liquid electrolyte may be encompassed by the hydrogel. Likewise, a hydrogel according to an embodiment of the invention may provide a substrate between two electrodes in an electrophoresis apparatus. The hydrogel may also be conducting. The hydrogel may also serve in enhancing the efficiency of charge-separated states and/or slowing down charge recombination. The hydrogel may thus be applied in any form photovoltaics, including a solar cell.

In some embodiments a hydrogel disclosed herein is a biocompatible, including a pharmaceutically acceptable hydrogel. The term "biocompatible" (which also can be referred to as "tissue compatible"), as used herein, is a hydrogel that produces little if any adverse biological response when used in vivo. The term thus generally refers to the inability of a hydrogel to promote a measurably adverse biological response in a cell, including in the body of an animal, including a human. A biocompatible hydrogel can have one or more of the following properties: non-toxic, non-mutagenic, non-allergenic, non-carcinogenic, and/or non-irritating. A biocompatible hydrogel, in the least, can be innocuous and tolerated by the respective cell and/or body. A biocompatible hydrogel, by itself, may also improve one or more functions in the body.

Depending on the amino acids that are included in the peptide/peptoid that is included in a hydrogel, a respective hydrogel may be biodegradable. A biodegradable hydrogel gradually disintegrates or is absorbed in vivo over a period of time, e.g., within months or years. Disintegration may for instance occur via hydrolysis, may be catalysed by an enzyme and may be assisted by conditions to which the hydrogel is exposed in a human or animal body, including a tissue, a blood vessel or a cell thereof. Where a peptide is made up entirely of natural amino acids, a respective peptide can usually be degraded by enzymes of the human/animal body.

A hydrogel according to an embodiment of the invention may also serve as a depot for a pharmaceutically active compound such as a drug. A hydrogel according to an embodiment of the invention may be designed to mimic the natural extracellular matrix of an organism such as the human or animal body. A fiber formed from the peptide/peptoid of an embodiment of the invention, including a respective hydrogel, may serve as a biological scaffold. A hydrogel of an embodiment of the invention may be included in an implant, in a contact lens or may be used in tissue engineering. In one embodiment, the peptides consist typically of 3-7 amino acids and are able to self-assemble into complex fibrous scaffolds which are seen as hydrogels, when dissolved in water or aqueous solution. These hydrogels can retain water up to 99.9% and possess sufficiently high mechanical strength. Thus, these hydrogels can act as artificial substitutes for a variety of natural tissues without the risk of immunogenicity. The hydrogels in accordance with the present invention may be used for cultivating suitable primary cells and thus establish an injectable cell-matrix compound in order to implant or reimplant the newly formed cell-matrix in vivo. Therefore, the hydrogels in accordance with the present invention are particularly useful for tissue regeneration or tissue engineering applications. As used herein, a reference to an "implant" or "implantation" refers to uses and applications of/for surgical or arthroscopic implantation of a hydrogel containing device into a human or animal, e.g. mammalian, body or limb. Arthroscopic techniques are taken herein as a subset of surgical techniques, and any reference to surgery, surgical, etc., includes arthroscopic techniques, methods and devices. A surgical implant that includes a hydrogel according to an embodiment of the invention may include a peptide and/or peptoid scaffold. This the peptide and/or peptoid scaffold may be defined by the respective hydrogel. A hydrogel of an embodiment of the invention may also be included in a wound cover such as gauze or a sheet, serving in maintaining the wound in a moist state to promote healing.

Depending on the amino acid sequence used in the peptide/peptoid the hydrogel may be temperature-sensitive. It may for instance have a lower critical solution temperature or a temperature range corresponding to such lower critical solution temperature, beyond which the gel collapses as hydrogen bonds by water molecules are released as water molecules are released from the gel.

The disclosed subject matter also provides improved chiral amphiphilic natural-based peptides and/or peptoids that assemble to peptide/peptoid hydrogels with very favorable material properties. The advantage of these peptide/peptoid hydrogels is that they are accepted by a variety of different primary human cells, thus providing peptide scaffolds that can be useful in the repair and replacement of various tissues. Depending on the chirality of the peptide monomer the character of the hydrogels can be designed to be more stable and less prone to degradation though still biocompatible.

A hydrogel and/or a peptide/peptoid described herein can be administered to an organism, including a human patient per se, or in pharmaceutical compositions where it may include or be mixed with pharmaceutically active ingredients or suitable carriers or excipient(s). Techniques for formulation and administration of respective hydrogels or peptides/peptoids resemble or are identical to those of low molecular weight compounds well established in the art. Exemplary routes include, but are not limited to, oral, transdermal, and parenteral delivery. A hydrogel or a peptide/peptoid may be used to fill a capsule or tube, or may be provided in compressed form as a pellet. The peptide/peptoid or the hydrogel may also be used in injectable or sprayable form, for instance as a suspension of a respective peptide/peptoid.

A hydrogel of an embodiment of the invention may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. It is noted in this regard that for administering microparticles a surgical procedure is not required. Where the microparticles include a biodegradable polymer there is no need for device removal after release of the anticancer agent. Nevertheless the microparticles may be included in or on a scaffold, a coating, a patch, composite material, a gel or a plaster.

In some embodiments one may administer a hydrogel and/or a peptide/peptoid in a local rather than systemic manner, for example, via injection.

Pharmaceutical compositions that include a hydrogel and/or a peptide/peptoid of an embodiment of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with an embodiment of the present invention thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the peptide/peptoid of an embodiment of the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the hydrogel and/or peptide/peptoid can be formulated readily by combining them with pharmaceutically acceptable carriers well known in the art. Such carriers enable the hydrogel and/or peptide/peptoid, as well as a pharmaceutically active compound, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The hydrogel and/or peptide/peptoid may be formulated for parenteral administration by injection, e.g., by intramuscular injections or bolus injection or continuous infusion. Formulations for injection may be presented in unit dosage form, e.g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

The hydrogel and/or peptide/peptoid may be formulated for other drug delivery systems like implants, or trandermal patches or stents.

EXAMPLES

Experiments have been performed to illustrate the technical aspects of exemplary embodiments of the present invention. The following examples are described in the Experimental Methods and Results. The skilled artisan will readily recognize that the examples are intended to be illustrative and are not intended to limit the scope of the present invention.
Experimental Methods and Results
Peptides The peptide sequences were designed to represent an amphiphilic peptide structure containing a hydrophilic head group and a hydrophobic tail. The rationale for the peptides design was to create a peptide monomer of decreasing size resembling a cone shaped structure. The hydrophobic tail differs by using different aliphatic amino acids. It is consisting of the following aliphatic amino acids such as glycine, alanine, valine, leucine and isoleucine and the hydrophilic head group is consisting of one or two polar or charged amino acids. The sequence order of the hydrophobic tail differed by using different aliphatic amino acids. The peptides were commercially synthesized from GL Biochem, Shanghai, China. In order to verify the reproducibility of the peptide hydrogel-forming behavior peptides were also synthesized from other companies (Biomatik Corp., Anaspec. Inc, USA). The peptides have a purity of equal or higher than 95% verified by High-performance liquid chromatography (HPLC) and mass spectrometry. The peptide stock solutions were dissolved in water at 5 to 10 mg/ml. Most of the peptides are acetylated at the N-terminus.
Peptide-Based Hydrogel Preparation.

All peptides (GL Biochem, Shanghai, China, ≥98% purity) were freshly prepared in order to avoid premature peptide aggregation. The peptides were dissolved in water and left at room temperature to form hydrogels. Depending on the peptide concentration, the self-assembly process occurred immediately, within hours or even within days (experimental time frame for gelation). For higher peptide concentrations peptides were dissolved in milliQ water by vortexing. If a forced and accelerated hydrogel preparation was needed, the peptide solution was subjected to sonication in a water bath (Barnstead Labline 9319 UltrasonicLC60H). No significant structural differences were observed between hydrogels produced via self-assembly and those whose assembly was facilitated by sonication. Few peptides formed hydrogels more easily at elevated temperatures, i.e. at 50° C.

To study the effect of concentration variation, both $AcLD_6$ (L) and AcID3 (L) hydrogels were prepared with varying concentration as specified above. To study the effect of monovalent and divalent cations, $AcLD_6$ (L) hydrogels were prepared by dissolving peptide in 10, 50, 100 and 150 mM NaCl and $CaCl_2$ solutions. FESEM and rheology studies were further performed to characterize the morphology and strength of these hydrogels.

Preparation of gelatin and collagen gels: Gelatin (Type A, G1890; Sigma Aldrich) hydrogels was prepared by first dissolving gelatin in milli Q water by heating followed by cooling till the gelation was observed. Collagen (Type I from bovine, Advanced Biomatrix, USA) was diluted with PBS buffer to a concentration of 1.5 mg/ml and titrated to pH 7.4 using 0.1M NaOH. Gelation was achieved by incubating the solution at 37° C. for 1 hour.
Circular Dichroism (CD) Spectroscopy Secondary peptide structures were analyzed by measuring ellipticity spectra using the Aviv Circular Dichroism Spectrometer, model 410. CD samples were prepared by diluting stock Peptides solutions (5-10 mg/ml) in water. The diluted peptide solutions were filled in to a cuvette with 1 mm path length and spectra were acquired. As a blank reference water was used and the reference was subtracted from the raw data before molar ellipticity was calculated. The calculation was based on the formula: $[\theta]_\lambda = \theta_{obs} \times 1/(10 \text{ Len})$, where $[\theta]_\lambda$ is the molar ellipticity at λ in deg cm² d/mol, is the observed ellipticity at λ in mdeg, L is the path length in cm, c is the concentration of the peptide in M, and n is the number of amino acids in the peptide. Secondary structure analysis was done using CDNN software.
Environmental Scanning Electron Microscopy (ESEM)

Samples were placed onto a sample holder of FEI Quanta 200 Environmental Scanning Electron Microscopy. The surface of interest was then examined using accelerating voltage of 10 kV at a temperature of 4° C.
Field Emission Scanning Electron Microscopy (FESEM)

Samples were frozen at −20° C. and subsequently to −80° C.: Frozen samples were further freeze dried. Freeze dried samples were fixed onto a sample holder using conductive tape and sputtered with platinum from both the top and the sides in a JEOL JFC-1600 High Resolution Sputter Coater. The coating current used was 30 mA and the process lasted for 60 sec. The surface of interest was then examined with a JEOL JSM-7400F Field Emission Scanning Electron Microscopy system using an accelerating voltage of 5-10 kV.

Rheological Measurements

To determine the viscoelastic properties of the peptide-based hydrogels, hydrogels were subjected to dynamic time, strain and frequency sweep experiments using the ARES-G2 rheometer (TA Instruments, Piscataway, N.J.) with the 25.0 mm diameter titanium parallel plate geometry and a 0.8 mm gap distance. Oscillatory frequency study was performed to compare the strength of peptide based hydrogel with varying concentration of peptides, or for peptide in presence of monovalent or divalent ions. Oscillatory frequency sweep studies were performed at 0.1-100 rad/s frequency and 0.1% strain at 25° C. and 50° C.

[A] Ac-LD$_6$ [L]:

Peptide sequence: Ac-LIVAGD-COOH

Molecular weight: 629.56

(1) Temperature sweep study for Ac-LD$_6$ (L):
  (a) The peptide mixture was then placed on rheometer lower plate. Following parameters were optimized:
    Gap between two plates: 1 mm
    Strain: 10%
    Frequency: 6.28 rad/sec
    Temperature scan: 4° C. to 60° C.
    Sample volume: 500 µl (2) Frequency sweep study for Ac-LD$_6$ (L):
  Optimized parameter required to perform frequency sweep study
    Gap between two plates: 0.8 mm
    Strain: 0.1%
    Temperature: 25 and 50° C.
    Sample volume: 1 ml
    Frequency scan: 0.1 rad/sec to 100 rad/sec
    Concentration of Ac-LD-6 (L) in hydrogel: 10 mg/ml (3) Effect of concentration variation of Ac-LD$_6$ (L) on gel strength:
  Optimized parameters that are required to perform frequency sweep studies for measuring gel strength are as follows:
    Gap between two plates: 0.8 mm
    Strain: 0.1%
    Temperature: 25 and 50° C.
    Sample volume: 1 ml
    Frequency scan: 0.1 rad/sec to 100 rad/sec
    Concentrations of Ac-LD$_6$ (L) in hydrogels: 5 mg/ml, 10 mg/ml, 15 mg/ml and, 20 mg/ml and 30 mg/ml in water.

(4) Effect of sodium chloride (NaCl) on the gel strength of Ac-LD$_6$ (L):
  Effect of sodium chloride on Ac-LD$_6$ (L) based hydrogels, were studied by performing a frequency sweep study on hydrogels prepared by dispersing 10 mg of Ac-LD-6 (L) in varying concentration of NaCl solution for example 10 mM, 50 mM, 100 mM and 150 mM of NaCl solution using optimized procedure to form hydrogels. Optimized parameter required to perform frequency sweep study to measure gel strength in presence of NaCl are as follows:
    Gap between two plates: 0.5 mm and 0.8 mm
    Strain: 10% and 0.1% respectively
    Temperature: 25° C. and 50° C.
    Sample volume: 1 ml
    Frequency scan: 0.1 rad/sec to 100 rad/sec
    Concentrations of NaCl solutions used to prepare 10 mg/ml of Ac-LD-6 (L) Hydrogels: 10 mM, 50 mM, 100 mM, 150 mM NaCl solution.

Cell Growth Experiments

In order to find out whether the peptide hydrogels can serve as a scaffold for tissue engineering, its biocompatibility was investigated. Different primary human cells were seeded on top of the hydrogel after its gelation in tissue culture medium (DMEM without serum) in 6-well, 24-well or 96-well culture plates, see the culture conditions below. During the next 2-4 days no change of medium was necessary, but eventually fresh media was added to the wells. The cells were analyzed for viability.

Primary human renal proximal tubule cells (HPTCs) and primary human umbilical vein endothelial cells (HUVECs) were obtained from ScienCell Research Laboratories (Carlsbad, Calif., USA). HPTCs were cultivated in basal epithelial cell medium supplemented with 2% fetal bovine serum (FBS) and 1% epithelial cell growth supplement (all components obtained from ScienCell Research Laboratories). The culture medium for I-IUVECs was endothelial cell medium containing 5% FBS and 1% endothelial cell growth supplement (ScienCell Research Laboratories). All cell culture media used were supplemented with 1% penicillin/streptomycin solution (ScienCell Research Laboratories), and all cells were cultivated at 37° C. in a 5% $CO_2$ atmosphere. The seeding density of the cells was about $5 \times 10^4$ cells/cm$^2$. However since HUVECs are bigger than HPTCs the cell number would be slightly lower than one for HPTC cells (~$4.5 \times 10^4$ cells/cm$^2$). Both cell types had a confluency of about 80% in the wells after seeding.

The listing or discussion of a previously published document in this specification should not necessarily be taken as an acknowledgement that the document is part of the state of the art or is common general knowledge. All documents listed are hereby incorporated herein by reference in their entirety for all purposes.

Exemplary embodiments of the invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An amphiphilic peptide and/or peptoid capable of forming a hydrogel, the amphiphilic peptide and/or peptoid comprising an amphiphilic sequence consisting of:
   a hydrophobic sequence stretch of n non repetitive aliphatic amino acids, such that two aliphatic amino acids coupled to each other are always different from one another, wherein n is an integer from 4 to 6, wherein all or a portion of the aliphatic amino acids of the hydrophobic sequence stretch are arranged in an order of decreasing amino acid size in the direction from N- to C-terminus of the amphiphilic peptide and/or peptoid, wherein the size of the aliphatic amino acids is defined as I=L>V>A>G, and
   a polar moiety linked to said hydrophobic sequence stretch which is acidic, neutral or basic, said polar moiety consisting of m adjacent hydrophilic amino acid, wherein m is 1,
   wherein said hydrophobic sequence stretch comprises and/or forms the N-terminus of the amphiphilic peptide and/or peptoid and said polar moiety consists of one amino acid positioned at the C-terminus of the amphiphilic peptide and/or peptoid,
   and wherein the N-terminus of the amphiphilic sequence carries a protecting group.

2. The amphiphilic peptide and/or peptoid of claim 1, wherein said aliphatic amino acids arranged in order of decreasing amino acid size have a sequence with a length of 4 to 5 amino acids.

3. The amphiphilic peptide and/or peptoid of claim 1, wherein said aliphatic amino acids arranged in an order of decreasing amino acid size have a sequence selected from LIVAG (SEQ ID NO: 43), ILVAG (SEQ ID NO: 44), LAVAG (SEQ ID NO: 46), IVAG (SEQ ID NO: 47), LIVA (SEQ ID NO: 48) and LIVG (SEQ ID NO: 49).

4. The amphiphilic peptide and/or peptoid of claim 1, wherein the amphiphilic sequence undergoes a conformational change during self-assembly, and the conformational change is concentration dependent.

5. The amphiphilic peptide and/or peptoid of claim 1, wherein the amphiphilic sequence is one of SEQ ID NO: 2-3, 6-8, 10, 11, 13-14, 17-21, 32, 35-36, or 39-41.

6. The amphiphilic peptide and/or peptoid of claim 1, wherein the protecting group is an acetyl group.

7. An amphiphilic peptide and/or peptoid capable of forming a hydrogel, the amphiphilic peptide and/or peptoid comprising an amphiphilic sequence consisting of:
   a hydrophobic sequence stretch having a sequence selected from LLLL (SEQ ID NO: 50), LL, VVVV (SEQ ID NO: 51), VV, AAAA (SEQ ID NO: 52), AAA, AA, GGGG (SEQ ID NO: 53), GGG, GG, LIVAG (SEQ ID NO: 43) and LIVAA (SEQ ID NO: 45),
   a polar moiety linked to said hydrophobic sequence stretch which is acidic, neutral or basic, said polar moiety comprising m adjacent hydrophilic amino acids, wherein m is an integer from 1 to 2,
   wherein said hydrophobic sequence stretch comprises and/or forms the N-terminus of the amphiphilic peptide and/or peptoid and said polar moiety consists of at least one amino acid positioned at the C-terminus of the amphiphilic peptide and/or peptoid,
   and wherein the N-terminus of the amphiphilic sequence carries a protecting group.

8. The amphiphilic peptide and/or peptoid of claim 7, wherein the amphiphilic sequence undergoes a conformational change during self-assembly, and the conformational change is concentration dependent.

9. The amphiphilic peptide and/or peptoid of claim 7, wherein the amphiphilic sequence is one of SEQ ID NO: 25-28, LIVAGDD (SEQ ID NO: 31), LIVAAD (SEQ ID NO: 33) or LIVAGEE (SEQ ID NO: 38).

10. The amphiphilic peptide and/or peptoid of claim 7, wherein the protecting group is an acetyl group.

11. An amphiphilic peptide and/or peptoid capable of forming a hydrogel, the amphiphilic peptide and/or peptoid comprising an amphiphilic sequence consisting of:
   a hydrophobic sequence stretch having a sequence AIVA (SEQ ID NO:54), and
   a polar moiety linked to said hydrophobic sequence stretch which is acidic, neutral or basic, said polar moiety comprising m adjacent hydrophilic amino acids, wherein m is an integer from 1 to 2,
   wherein said hydrophobic sequence stretch comprises and/or forms the N-terminus of the amphiphilic peptide and/or peptoid and said polar moiety consists of at least one amino acid positioned at the C-terminus of the amphiphilic peptide and/or peptoid,
   and wherein the N-terminus of the amphiphilic sequence carries a protecting group.

12. The amphiphilic peptide and/or peptoid of claim 11, wherein the amphiphilic sequence undergoes a conformational change during self-assembly, and the conformational change is concentration dependent.

13. The amphiphilic peptide and/or peptoid of claim 11, wherein the amphiphilic sequence is one of SEQ ID NO: 4-5, 12, 15, 34 or 37.

14. The amphiphilic peptide and/or peptoid of claim 11, wherein the protecting group is an acetyl group.

15. The amphiphilic peptide and/or peptoid of claim 1, wherein the amphiphilic sequence is LIVAGD (SEQ ID NO: 2 or 3).

16. The amphiphilic peptide and/or peptoid of claim 1, wherein the amphiphilic sequence is ILVAGD (SEQ ID NO: 6 or 7).

17. The amphiphilic peptide and/or peptoid of claim 1, wherein the amphiphilic sequence is LIVAGK (SEQ ID NO: 19 or 39).

18. The amphiphilic peptide and/or peptoid of claim 1, wherein the amphiphilic sequence is LIVAGS (SEQ ID NO: 10 or 11).

19. An amphiphilic peptide and/or peptoid capable of forming a hydrogel, the amphiphilic peptide and/or peptoid comprising an amphiphilic sequence which is IVAD (SEQ ID NO: 22 or 23), and wherein the N-terminus of the amphiphilic sequence carries a protecting group.

20. The amphiphilic peptide and/or peptoid of claim 19, wherein the protecting group is an acetyl group.

21. An amphiphilic peptide and/or peptoid capable of forming a hydrogel, the amphiphilic peptide and/or peptoid comprising an amphiphilic sequence consisting of a hydrophobic sequence stretch of two aliphatic amino acids which are arranged in an order of decreasing amino acid size in the direction from N- to C-terminus of the amphiphilic peptide and/or peptoid, wherein the size of the aliphatic amino acids is defined as I=L>V>A>G, and one adjacent hydrophilic amino acid, wherein said hydrophobic sequence stretch comprises and/or forms the N-terminus of the amphiphilic peptide and/or peptoid and said one hydrophilic amino acid is positioned at the C-terminus of the amphiphilic peptide and/or peptoid, and wherein the N-terminus of the amphiphilic sequence carries an acetyl group.

22. The amphiphilic peptide and/or peptoid of claim 21, wherein the hydrophobic sequence stretch of two aliphatic amino acids is IV.

23. The amphiphilic peptide and/or peptoid of claim 21, wherein the amphiphilic sequence is IVD (SEQ ID NO: 24 or 42).

24. The amphiphilic peptide and/or peptoid of claim 10, wherein the amphiphilic sequence is Ac-LIVAGDD (SEQ ID NO:1), Ac-LIVAAD (SEQ ID NO:9) or Ac-LIVAGEE (SEQ ID NO:16).

* * * * *

SEQUENCE LISTING

<160> NUMBER OF SEQ ID NOS: 54

<210> SEQ ID NO 1
<211> LENGTH: 7
<212> TYPE: PRT
<213> ORGANISM: Artificial Sequence
<220> FEATURE:
<223> OTHER INFORMATION: Synthesized

<400> SEQUENCE: 1

Leu Ile Val Ala Gly Asp Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthesized

<400> SEQUENCE: 2

Leu Ile Val Ala Gly Asp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Asp

<400> SEQUENCE: 3

Xaa Xaa Xaa Xaa Gly Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthesized

<400> SEQUENCE: 4

Ala Ile Val Ala Gly Asp
1               5

<210> SEQ ID NO 5
<211> LENGTH: 6
<212> TYPE: PRT
<213> ORGANISM: Artificial Sequence

```
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ala
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Asp

<400> SEQUENCE: 5

Xaa Xaa Xaa Xaa Gly Xaa
1               5

<210> SEQ ID NO 6
<211> LENGTH: 6
<212> TYPE: PRT
<213> ORGANISM: Artificial Sequence
<220> FEATURE:
<223> OTHER INFORMATION: Synthesized

<400> SEQUENCE: 6

Ile Leu Val Ala Gly Asp
1               5

<210> SEQ ID NO 7
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Leu
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Asp

<400> SEQUENCE: 7

Xaa Xaa Xaa Xaa Gly Xaa
1               5

<210> SEQ ID NO 8
<211> LENGTH: 6
<212> TYPE: PRT
<213> ORGANISM: Artificial Sequence
```

```
<220> FEATURE:
<223> OTHER INFORMATION: Synthesized

<400> SEQUENCE: 8

Leu Ala Val Ala Gly Asp
1               5

<210> SEQ ID NO 9
<211> LENGTH: 6
<212> TYPE: PRT
<213> ORGANISM: Artificial Sequence
<220> FEATURE:
<223> OTHER INFORMATION: Synthesized

<400> SEQUENCE: 9

Leu Ile Val Ala Ala Asp
1               5

<210> SEQ ID NO 10
<211> LENGTH: 6
<212> TYPE: PRT
<213> ORGANISM: Artificial Sequence
<220> FEATURE:
<223> OTHER INFORMATION: Synthesized

<400> SEQUENCE: 10

Leu Ile Val Ala Gly Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Ser

<400> SEQUENCE: 11

Xaa Xaa Xaa Xaa Gly Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized

<400> SEQUENCE: 12

Ala Ile Val Ala Gly Ser
1               5
```

<210> SEQ ID NO 13
<211> LENGTH: 6
<212> TYPE: PRT
<213> ORGANISM: Artificial Sequence
<220> FEATURE:
<223> OTHER INFORMATION: Synthesized

<400> SEQUENCE: 13

Ile Leu Val Ala Gly Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized

<400> SEQUENCE: 14

Leu Ile Val Ala Gly Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized

<400> SEQUENCE: 15

Ala Ile Val Ala Gly Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Synthesized

<400> SEQUENCE: 16

Leu Ile Val Ala Gly Glu Glu
1               5

<210> SEQ ID NO 17
<211> LENGTH: 6
<212> TYPE: PRT
<213> ORGANISM: Artificial Sequence
<220> FEATURE:
<223> OTHER INFORMATION: Synthesized

<400> SEQUENCE: 17

Leu Ile Val Ala Gly Glu
1               5

<210> SEQ ID NO 18
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE

```
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Glu

<400> SEQUENCE: 18

Xaa Xaa Xaa Xaa Gly Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: Synthesized

<400> SEQUENCE: 19

Leu Ile Val Ala Gly Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Synthesized

<400> SEQUENCE: 20

Leu Ile Val Ala Asp
1               5

<210> SEQ ID NO 21
<211> LENGTH: 5
<212> TYPE: PRT
<213> ORGANISM: Artificial Sequence
<220> FEATURE:
<223> OTHER INFORMATION: Synthesized

<400> SEQUENCE: 21

Leu Ile Val Gly Asp
1               5

<210> SEQ ID NO 22
<211> LENGTH: 4
<212> TYPE: PRT
<213> ORGANISM: Artificial Sequence
<220> FEATURE:
<223> OTHER INFORMATION: Synthesized

<400> SEQUENCE: 22

Ile Val Ala Asp
1

<210> SEQ ID NO 23
<211> LENGTH: 4
<212> TYPE: PRT
<213> ORGANISM: Artificial Sequence
<220> FEATURE:
<223> OTHER INFORMATION: Synthesized
```

```
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Val
<220> FEATURE:
<221> NAME/KEY: MISC_FEATURE
<222> LOCATION: (3)..(3)
<223> OTHER INFORMATION: D-form of Ala
<220> FEATURE:
<221> NAME/KEY: MISC_FEATURE
<222> LOCATION: (4)..(4)
<223> OTHER INFORMATION: D-form of Asp

<400> SEQUENCE: 23

Xaa Xaa Xaa Xaa
1

<210> SEQ ID NO 24
<211> LENGTH: 3
<212> TYPE: PRT
<213> ORGANISM: Artificial Sequence
<220> FEATURE:
<223> OTHER INFORMATION: Synthesized

<400> SEQUENCE: 24

Ile Val Asp
1

<210> SEQ ID NO 25
<211> LENGTH: 4
<212> TYPE: PRT
<213> ORGANISM: Artificial Sequence
<220> FEATURE:
<223> OTHER INFORMATION: Synthesized

<400> SEQUENCE: 25

Ile Ile Ile Asp
1

<210> SEQ ID NO 26
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Ile
<220> FEATURE:
<221> NAME/KEY: MISC_FEATURE
<222> LOCATION: (4)..(4)
<223> OTHER INFORMATION: D-form of Asp

<400> SEQUENCE: 26

Xaa Xaa Xaa Xaa
1

<210> SEQ ID NO 27
```

```
<211> LENGTH: 4
<212> TYPE: PRT
<213> ORGANISM: Artificial Sequence
<220> FEATURE:
<223> OTHER INFORMATION: Synthesized

<400> SEQUENCE: 27

Ile Ile Ile Lys
1

<210> SEQ ID NO 28
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Ile
<220> FEATURE:
<221> NAME/KEY: MISC_FEATURE
<222> LOCATION: (4)..(4)
<223> OTHER INFORMATION: D-form of Lys

<400> SEQUENCE: 28

Xaa Xaa Xaa Xaa
1

<210> SEQ ID NO 29
<211> LENGTH: 3
<212> TYPE: PRT
<213> ORGANISM: Artificial Sequence
<220> FEATURE:
<223> OTHER INFORMATION: Synthesized

<400> SEQUENCE: 29

Ile Ile Asp
1

<210> SEQ ID NO 30
<211> LENGTH: 3
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Asp

<400> SEQUENCE: 30

Xaa Xaa Xaa
1
```

```
<210> SEQ ID NO 31
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Asp
<220> FEATURE:
<221> NAME/KEY: MISC_FEATURE
<222> LOCATION: (7)..(7)
<223> OTHER INFORMATION: D-form of Asp

<400> SEQUENCE: 31

Xaa Xaa Xaa Xaa Gly Xaa Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ala
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Asp

<400> SEQUENCE: 32

Xaa Xaa Xaa Xaa Gly Xaa
1               5

<210> SEQ ID NO 33
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
```

-continued

```
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (5)..(5)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Asp

<400> SEQUENCE: 33

Xaa Xaa Xaa Xaa Xaa Xaa
1               5

<210> SEQ ID NO 34
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ala
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Ser

<400> SEQUENCE: 34

Xaa Xaa Xaa Xaa Gly Xaa
1               5

<210> SEQ ID NO 35
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Leu
<220> FEATURE:
<221> NAME/KEY: MISC_FEATURE
<222> LOCATION: (3)..(3)
<223> OTHER INFORMATION: D-form of Val
```

```
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Ser

<400> SEQUENCE: 35

Xaa Xaa Xaa Xaa Gly Xaa
1               5

<210> SEQ ID NO 36
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Thr

<400> SEQUENCE: 36

Xaa Xaa Xaa Xaa Gly Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ala
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Thr

<400> SEQUENCE: 37

Xaa Xaa Xaa Xaa Gly Xaa
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Glu
<220> FEATURE:
<221> NAME/KEY: MISC_FEATURE
<222> LOCATION: (7)..(7)
<223> OTHER INFORMATION: D-form of Glu

<400> SEQUENCE: 38

Xaa Xaa Xaa Xaa Gly Xaa Xaa
1               5

<210> SEQ ID NO 39
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (6)..(6)
<223> OTHER INFORMATION: D-form of Lys

<400> SEQUENCE: 39

Xaa Xaa Xaa Xaa Gly Xaa
1               5

<210> SEQ ID NO 40
<211> LENGTH: 5
<212> TYPE: PRT
<213> ORGANISM: Artificial Sequence
<220> FEATURE:
<223> OTHER INFORMATION: Synthesized
<220> FEATURE:
```

```
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (4)..(4)
<223> OTHER INFORMATION: D-form of Ala
<220> FEATURE:
<221> NAME/KEY: MISC_FEATURE
<222> LOCATION: (5)..(5)
<223> OTHER INFORMATION: D-form of Asp

<400> SEQUENCE: 40

Xaa Xaa Xaa Xaa Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Leu
<220> FEATURE:
<221> NAME/KEY: MISC_FEATURE
<222> LOCATION: (2)..(2)
<223> OTHER INFORMATION: D-form of Ile
<220> FEATURE:
<221> NAME/KEY: MISC_FEATURE
<222> LOCATION: (3)..(3)
<223> OTHER INFORMATION: D-form of Val
<220> FEATURE:
<221> NAME/KEY: MISC_FEATURE
<222> LOCATION: (5)..(5)
<223> OTHER INFORMATION: D-form of Asp

<400> SEQUENCE: 41

Xaa Xaa Xaa Gly Xaa
1               5

<210> SEQ ID NO 42
<211> LENGTH: 3
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: D-form of Ile
<220> FEATURE:
<221> NAME/KEY: MISC_FEATURE
<222> LOCATION: (2)..(2)
<223> OTHER INFORMATION: D-form of Val
<220> FEATURE:
<221> NAME/KEY: MISC_FEATURE
<222> LOCATION: (3)..(3)
<223> OTHER INFORMATION: D-form of Asp

<400> SEQUENCE: 42

Xaa Xaa Xaa
1
```

```
<210> SEQ ID NO 43
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Leu
<220> FEATURE:
<221> NAME/KEY: MISC_FEATURE
<222> LOCATION: (2)..(2)
<223> OTHER INFORMATION: L-form or D-form of Ile
<220> FEATURE:
<221> NAME/KEY: MISC_FEATURE
<222> LOCATION: (3)..(3)
<223> OTHER INFORMATION: L-form or D-form of Val
<220> FEATURE:
<221> NAME/KEY: MISC_FEATURE
<222> LOCATION: (4)..(4)
<223> OTHER INFORMATION: L-form or D-form of Ala

<400> SEQUENCE: 43

Xaa Xaa Xaa Xaa Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Ile
<220> FEATURE:
<221> NAME/KEY: MISC_FEATURE
<222> LOCATION: (2)..(2)
<223> OTHER INFORMATION: L-form or D-form of Leu
<220> FEATURE:
<221> NAME/KEY: MISC_FEATURE
<222> LOCATION: (3)..(3)
<223> OTHER INFORMATION: L-form or D-form of Val
<220> FEATURE:
<221> NAME/KEY: MISC_FEATURE
<222> LOCATION: (4)..(4)
<223> OTHER INFORMATION: L-form or D-form of Ala

<400> SEQUENCE: 44

Xaa Xaa Xaa Xaa Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Leu
<220> FEATURE:
<221> NAME/KEY: MISC_FEATURE
<222> LOCATION: (2)..(2)
<223> OTHER INFORMATION: L-form or D-form of Ile
<220> FEATURE:
<221> NAME/KEY: MISC_FEATURE
<222> LOCATION: (3)..(3)
<223> OTHER INFORMATION: L-form or D-form of Val
<220> FEATURE:
<221> NAME/KEY: MISC_FEATURE
```

-continued

```
<222> LOCATION: (4)..(4)
<223> OTHER INFORMATION: L-form or D-form of Ala
<220> FEATURE:
<221> NAME/KEY: MISC_FEATURE
<222> LOCATION: (5)..(5)
<223> OTHER INFORMATION: L-form or D-form of Ala

<400> SEQUENCE: 45

Xaa Xaa Xaa Xaa Xaa
1               5

<210> SEQ ID NO 46
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Leu
<220> FEATURE:
<221> NAME/KEY: MISC_FEATURE
<222> LOCATION: (2)..(2)
<223> OTHER INFORMATION: L-form or D-form of Ala
<220> FEATURE:
<221> NAME/KEY: MISC_FEATURE
<222> LOCATION: (3)..(3)
<223> OTHER INFORMATION: L-form or D-form of Val
<220> FEATURE:
<221> NAME/KEY: MISC_FEATURE
<222> LOCATION: (4)..(4)
<223> OTHER INFORMATION: L-form or D-form of Ala

<400> SEQUENCE: 46

Xaa Xaa Xaa Xaa Gly
1               5

<210> SEQ ID NO 47
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Ile
<220> FEATURE:
<221> NAME/KEY: MISC_FEATURE
<222> LOCATION: (2)..(2)
<223> OTHER INFORMATION: L-form or D-form of Val
<220> FEATURE:
<221> NAME/KEY: MISC_FEATURE
<222> LOCATION: (3)..(3)
<223> OTHER INFORMATION: L-form or D-form of Ala

<400> SEQUENCE: 47

Xaa Xaa Xaa Gly
1

<210> SEQ ID NO 48
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Leu
<220> FEATURE:
<221> NAME/KEY: MISC_FEATURE
```

```
<222> LOCATION: (2)..(2)
<223> OTHER INFORMATION: L-form or D-form of Ile
<220> FEATURE:
<221> NAME/KEY: MISC_FEATURE
<222> LOCATION: (3)..(3)
<223> OTHER INFORMATION: L-form or D-form of Val
<220> FEATURE:
<221> NAME/KEY: MISC_FEATURE
<222> LOCATION: (4)..(4)
<223> OTHER INFORMATION: L-form or D-form of Ala

<400> SEQUENCE: 48

Xaa Xaa Xaa Xaa
1

<210> SEQ ID NO 49
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Leu
<220> FEATURE:
<221> NAME/KEY: MISC_FEATURE
<222> LOCATION: (2)..(2)
<223> OTHER INFORMATION: L-form or D-form of Ile
<220> FEATURE:
<221> NAME/KEY: MISC_FEATURE
<222> LOCATION: (3)..(3)
<223> OTHER INFORMATION: L-form or D-form of Val

<400> SEQUENCE: 49

Xaa Xaa Xaa Gly
1

<210> SEQ ID NO 50
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Leu
<220> FEATURE:
<221> NAME/KEY: MISC_FEATURE
<222> LOCATION: (2)..(2)
<223> OTHER INFORMATION: L-form or D-form of Leu
<220> FEATURE:
<221> NAME/KEY: MISC_FEATURE
<222> LOCATION: (3)..(3)
<223> OTHER INFORMATION: L-form or D-form of Leu
<220> FEATURE:
<221> NAME/KEY: MISC_FEATURE
<222> LOCATION: (4)..(4)
<223> OTHER INFORMATION: L-form or D-form of Leu

<400> SEQUENCE: 50

Xaa Xaa Xaa Xaa
1

<210> SEQ ID NO 51
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
```

<222> LOCATION: (1)..(1)
<223> OTHER INFORMATION: L-form or D-form of Val
<220> FEATURE:
<221> NAME/KEY: MISC_FEATURE
<222> LOCATION: (2)..(2)
<223> OTHER INFORMATION: L-form or D-form of Val
<220> FEATURE:
<221> NAME/KEY: MISC_FEATURE
<222> LOCATION: (3)..(3)
<223> OTHER INFORMATION: L-form or D-form of Val
<220> FEATURE:
<221> NAME/KEY: MISC_FEATURE
<222> LOCATION: (4)..(4)
<223> OTHER INFORMATION: L-form or D-form of Val

<400> SEQUENCE: 51

Xaa Xaa Xaa Xaa
1

<210> SEQ ID NO 52
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Ala
<220> FEATURE:
<221> NAME/KEY: MISC_FEATURE
<222> LOCATION: (2)..(2)
<223> OTHER INFORMATION: L-form or D-form of Ala
<220> FEATURE:
<221> NAME/KEY: MISC_FEATURE
<222> LOCATION: (3)..(3)
<223> OTHER INFORMATION: L-form or D-form of Ala
<220> FEATURE:
<221> NAME/KEY: MISC_FEATURE
<222> LOCATION: (4)..(4)
<223> OTHER INFORMATION: L-form or D-form of Ala

<400> SEQUENCE: 52

Xaa Xaa Xaa Xaa
1

<210> SEQ ID NO 53
<211> LENGTH: 4
<212> TYPE: PRT
<213> ORGANISM: Artificial Sequence
<220> FEATURE:
<223> OTHER INFORMATION: Synthesized

<400> SEQUENCE: 53

Gly Gly Gly Gly
1

<210> SEQ ID NO 54
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: L-form or D-form of Ala
<220> FEATURE:
<221> NAME/KEY: MISC_FEATURE
<222> LOCATION: (2)..(2)
<223> OTHER INFORMATION: L-form or D-form of Ile
<220> FEATURE:
<221> NAME/KEY: MISC_FEATURE

```
<222> LOCATION: (3)..(3)
<223> OTHER INFORMATION: L-form or D-form of Val
<220> FEATURE:
<221> NAME/KEY: MISC_FEATURE
<222> LOCATION: (4)..(4)
<223> OTHER INFORMATION: L-form or D-form of Ala

<400> SEQUENCE: 54

Xaa Xaa Xaa Xaa
1
```